(12) United States Patent
Spotnitz et al.

(10) Patent No.: US 8,938,310 B2
(45) Date of Patent: Jan. 20, 2015

(54) CORONARY SINUS CANNULA WITH LEFT VENTRICLE LEAD AND PRESSURE TENT

(75) Inventors: Henry M. Spotnitz, New York, NY (US); Daniel Y. Wang, New York, NY (US); Santos Cabreriza, Dumont, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 268 days.

(21) Appl. No.: 13/381,046

(22) PCT Filed: Jul. 7, 2010

(86) PCT No.: PCT/US2010/041139
§ 371 (c)(1),
(2), (4) Date: Dec. 27, 2011

(87) PCT Pub. No.: WO2011/005814
PCT Pub. Date: Jan. 13, 2011

(65) Prior Publication Data
US 2012/0097174 A1    Apr. 26, 2012

Related U.S. Application Data

(60) Provisional application No. 61/223,603, filed on Jul. 7, 2009, provisional application No. 61/304,221, filed on Feb. 12, 2010, provisional application No. 61/318,682, filed on Mar. 29, 2010.

(51) Int. Cl.
*A61N 1/05* (2006.01)

(52) U.S. Cl.
CPC .......... *A61N 1/056* (2013.01); *A61N 2001/0585* (2013.01)
USPC .............................. 607/122; 607/115; 607/125

(58) Field of Classification Search
CPC ................ A61M 2025/0161; A61M 25/0108; A61N 1/056; A61N 2001/0585
USPC .............. 600/372–374, 433, 434; 607/9, 116, 607/122, 125, 115; 606/129
See application file for complete search history.

(56) References Cited

U.S. PATENT DOCUMENTS 5,728,148 A * 3/1998 Bostrom et al. ............... 607/116
5,755,760 A * 5/1998 Maguire et al. ............... 607/122
(Continued)

OTHER PUBLICATIONS

J. H. Artrip et al., "Transesophageal echocardiography guided placement of a CS pacing lead", "Annals of Thoracic Surgery", 2002, pp. 1254-1256, vol. 74, Publisher: Elsevier Science, Published in: Amsterdam/NL.

(Continued)

*Primary Examiner* — Allen Porter, Jr.
(74) *Attorney, Agent, or Firm* — Evans & Molinelli PLLC; Eugene J. Molinelli

(57) ABSTRACT

Techniques for biventricular pacing include a rigid shaped stylet approximating curves of a coronary sinus and branch vein. Some techniques include a parasternal coronary sinus cannula comprising an outer sheath and an obturator. The obturator is removeably disposed inside the outer sheath from a device end of the hollow shaft. The obturator includes a flexible stem that fits snugly inside the hollow shaft, a malleable core disposed inside the flexible stem, a tapered tip that extends beyond a cardiac end of the shaft when the obturator is disposed inside the outer sheath, and a sensor for determining properties of the subject in a vicinity of the tapered tip. An optional pressure-seal, such as a tent, connected to suction maintains negative intrepleural pressure for insertion under local anesthesia.

14 Claims, 15 Drawing Sheets

(56) References Cited

U.S. PATENT DOCUMENTS

| | | | |
|---|---|---|---|
| 5,879,295 A * | 3/1999 | Li et al. | 600/373 |
| 5,882,333 A * | 3/1999 | Schaer et al. | 604/95.01 |
| 5,999,858 A * | 12/1999 | Sommer et al. | 607/122 |
| 6,321,123 B1 * | 11/2001 | Morris et al. | 607/122 |
| 6,656,109 B2 | 12/2003 | DeVries et al. | |
| 6,907,298 B2 * | 6/2005 | Smits et al. | 607/125 |
| 7,257,450 B2 | 8/2007 | Auth et al. | |
| 7,551,967 B1 | 6/2009 | Karicherla et al. | |
| 2001/0044568 A1 | 11/2001 | Langberg et al. | |
| 2003/0130712 A1 * | 7/2003 | Smits et al. | 607/116 |
| 2004/0162601 A1 | 8/2004 | Smits | |
| 2005/0033111 A1 | 2/2005 | Taylor | |

OTHER PUBLICATIONS

J. W. Calvin, et al., "Permanent atrial pacing. Epicardial approach—pinch-on electrodes", "Archives of Surgery", 1976, pp. 712-715, vol. 11, No. 6, Publisher: American Medical Association, Published in: http://archsurg.ama-assn.org/cgi/reprint/111/6/712.

S. Cazeau et al., "Effects of multisite biventricular pacing in patients with heart failure and intraventricular conduction delay", "New England Journal of Medicine", 2001, pp. 873-880, vol. 344, Publisher: Massachusetts Medical Society, Published in: Boston, MA/US.

J. G. Cleland et al., "The effect of cardiac resynchronization on morbidity and mortality in heart failure", "New England Journal of Medicine", 2005, pp. 1539-1549, vol. 352, Publisher: Massachusetts Medical Society, Published in: Boston, MA/US.

A. E. Epstein et al., "ACC/AHA/HRS 2008 Guidelines for device-based therapy of cardiac rhythm abnormalities", "Circulation", May 15, 2008, pp. e350-e408, vol. 117, Publisher: American Heart Association, Published in: Boston, MA/US.

M. Fatemi et al., "Short and long-term single-centre experience with an S-shaped unipolar lead for left ventricular pacing", "Europace", 2003, pp. 207-211, vol. 5, Publisher: European Society of Cardiology, Published in: Sophia Antipolis/FR.

US International Search Authority, "ISRWO for PCT/US2010/041139", Mar. 9, 2010, pp. 1-8, Published in: USA.

J. M. Morgan and V. Delgado, "Lead positioning for cardiac resynchronization therapy: techniques and priorities", "Europace", 2009, pp. 22-28, vol. 11, No. 5, Publisher: European Society of Cardiology, Published in: http://europace.oxfordjournals.org/content/11/suppl_5/v22.full.

H. Negele et al., "What can happen during coronary sinus lead implantation: dislocation, perforation and other catastrophes", "Herzschrittmacherther Elektrophysiol", 2007, pp. 243-249, vol. 18, No. 4, Publisher: SpringerLink, Published in: http://www.springerlink.com/content/514g1868754227kr/.

J. L. Navia et al., "Minimally invasive left ventricular epicardial lead placement: surgical techniques for heart failure resynchronization t", "Annals of Thoracic Surgery", 2005, pp. 1536-1544, vol. 79, Publisher: Elsevier Sciences, Published in: Amsterdam/NL T. A. Quinn et al., "Simultaneous variation of ventricular pacing site and timing with biventricular pacing in acute ventricular failure impr", "American Journal of Physiology—Heart and Circulatory Physiology", Dec. 1, 2009, pp. H2220-H2226, vol. 297, No. 6, Publisher: American Physiological Society, Published in: http://ajpheart.physiology.org/content/297/6/H2220.full.

K. Toutouzas et al., "Coronary sinus thermography in idiopathic dilated cardiomyopathy: correlation with systemic inflammation and left ventri", "European Journal of Heart Failure", 2007, pp. 168-172, vol. 9, No. 2, Publisher: Oxford Journals, Published in: http://eurjhf.oxfordjournals.org/content19/2/168.full.

* cited by examiner

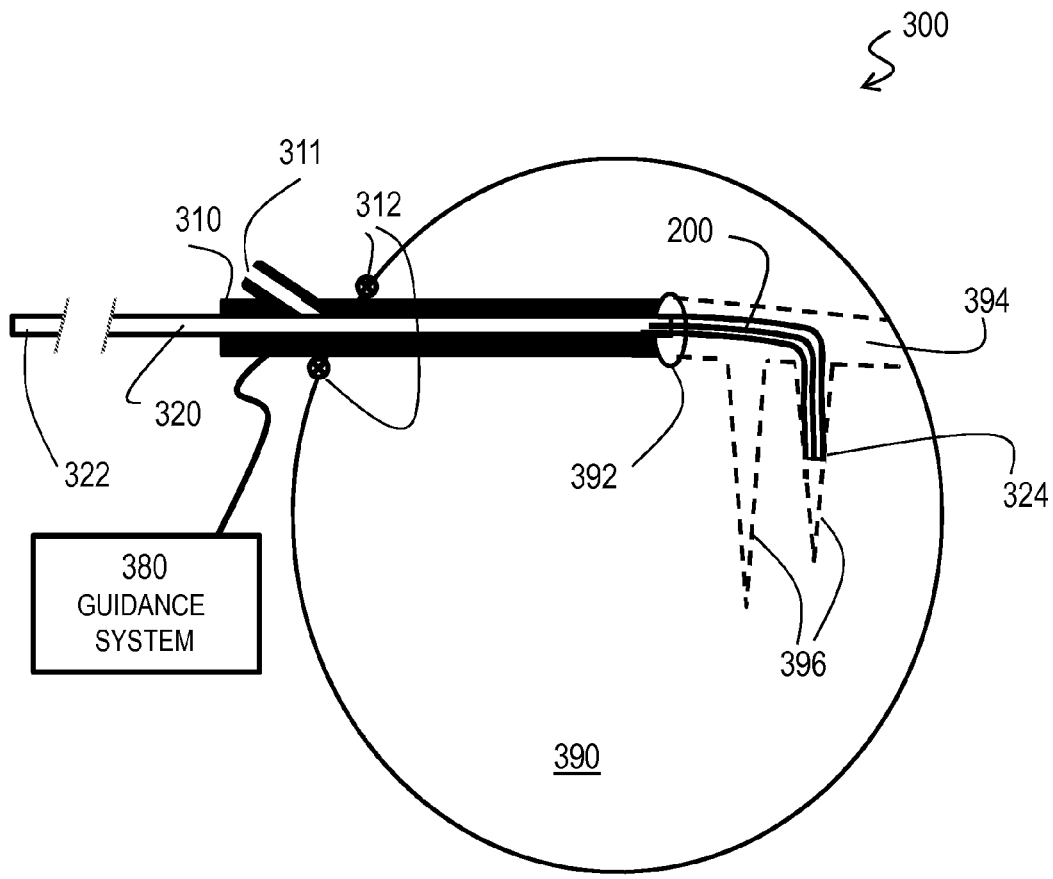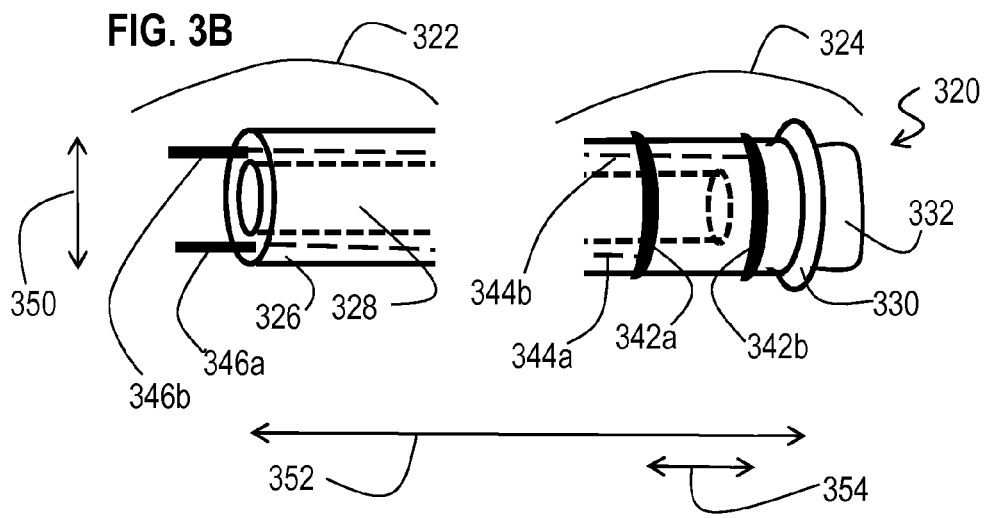

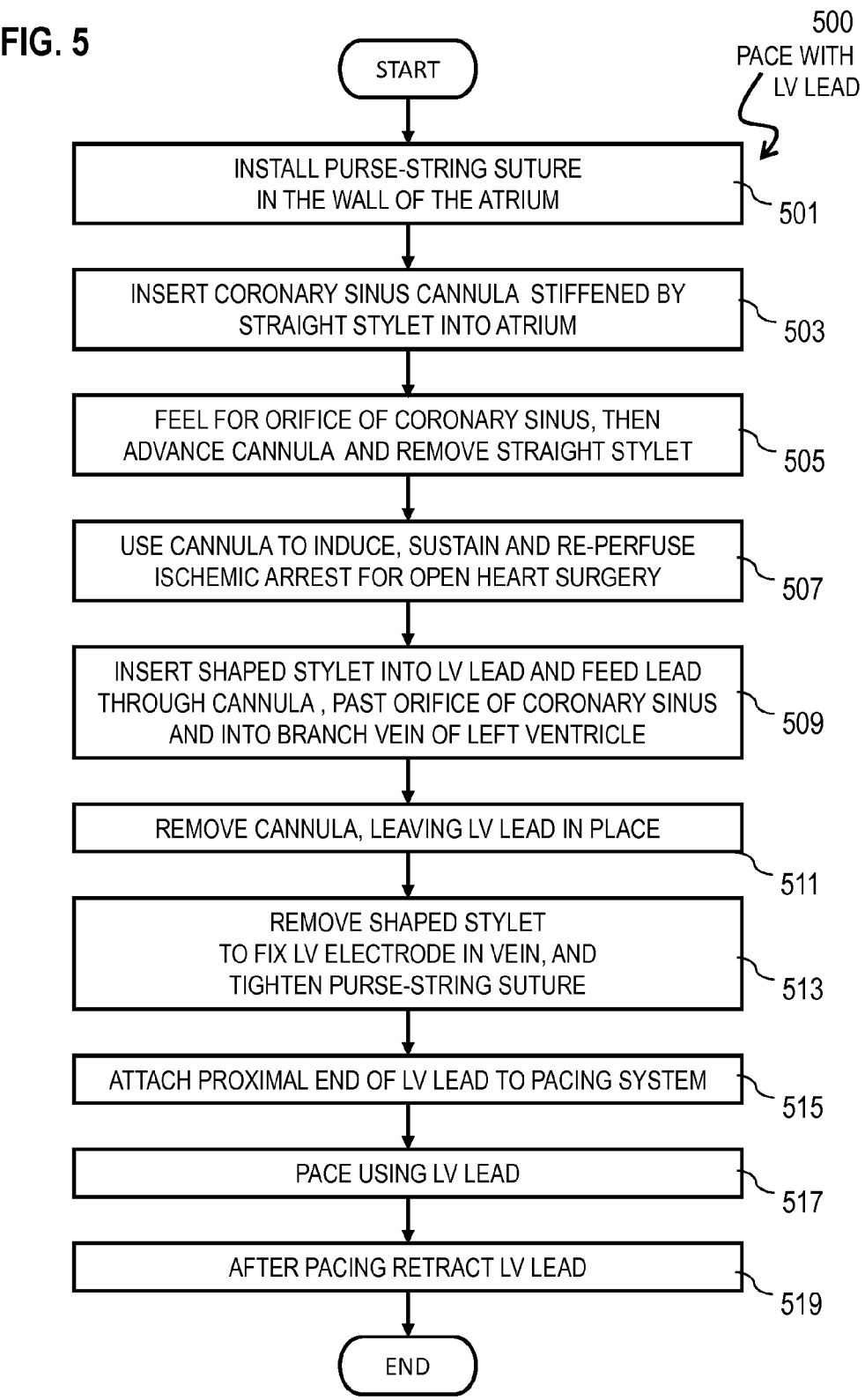

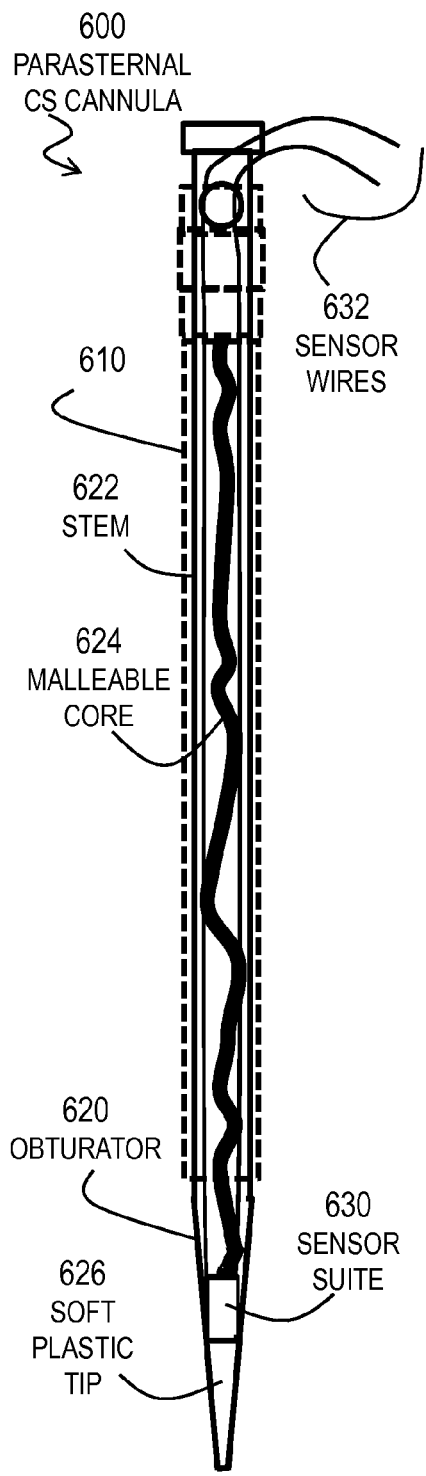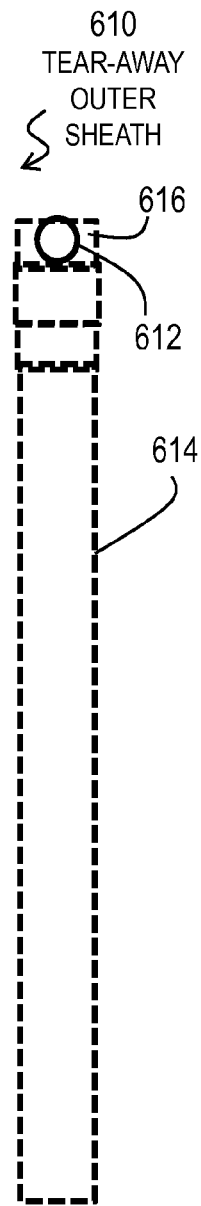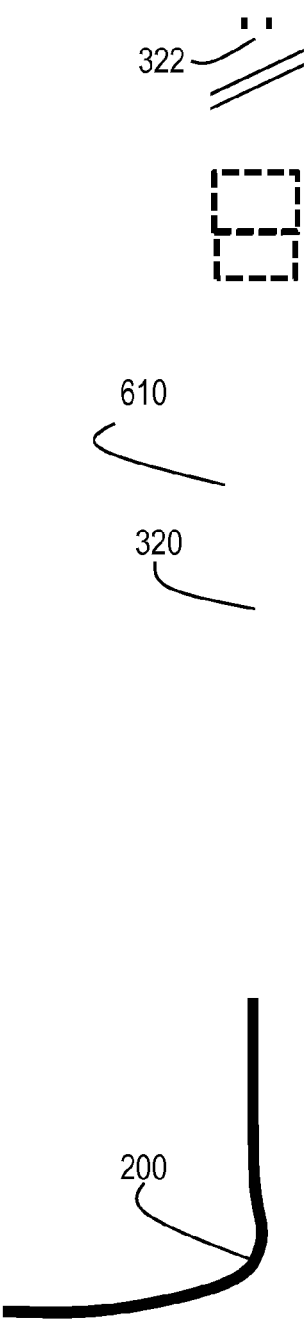

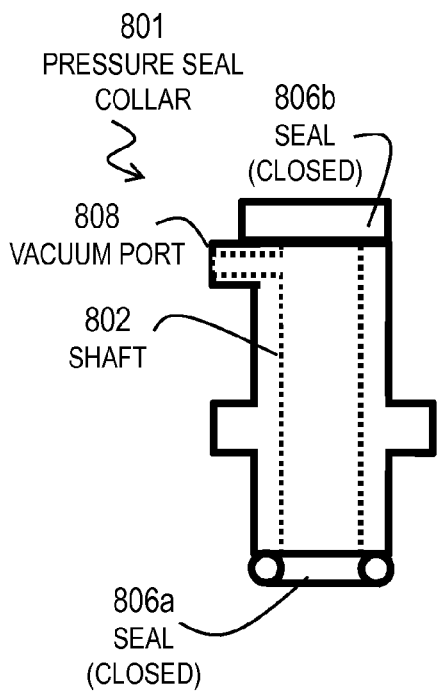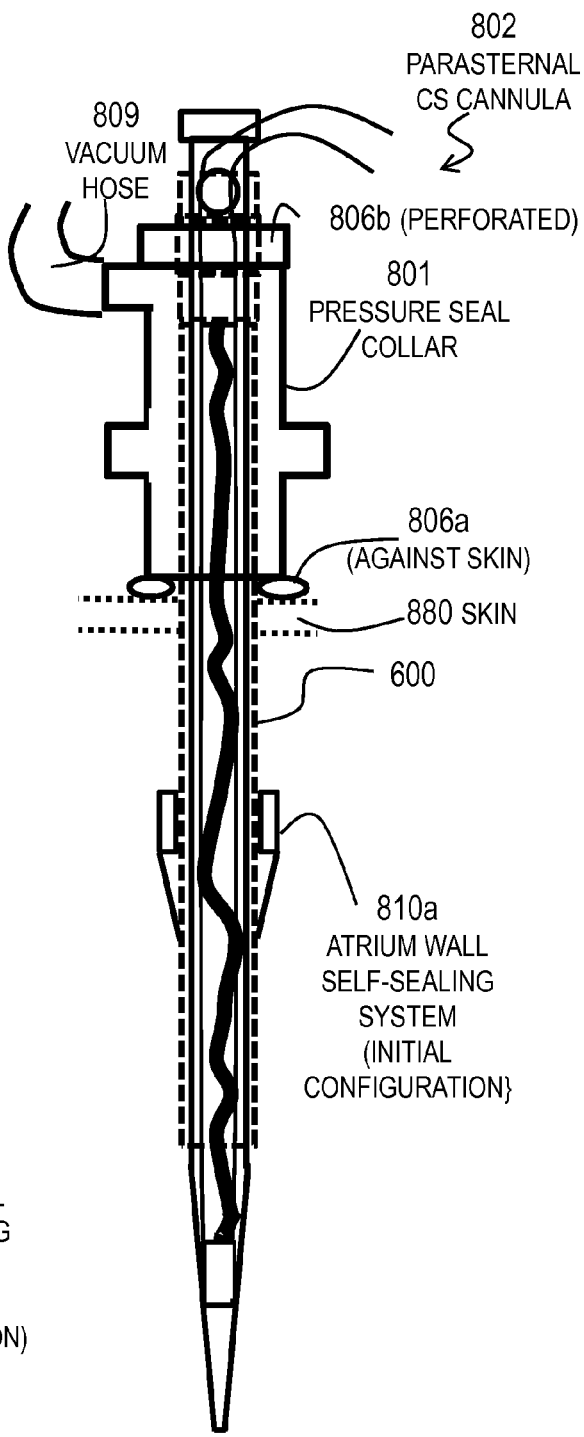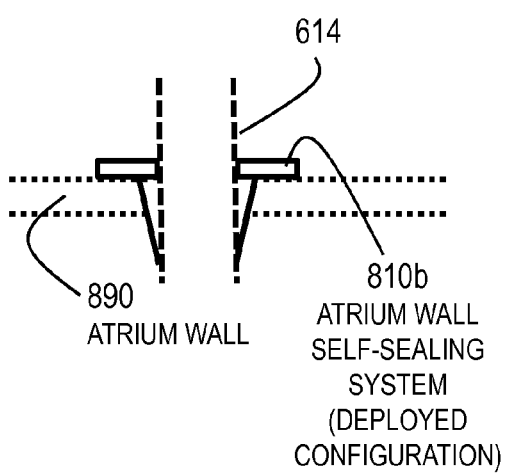

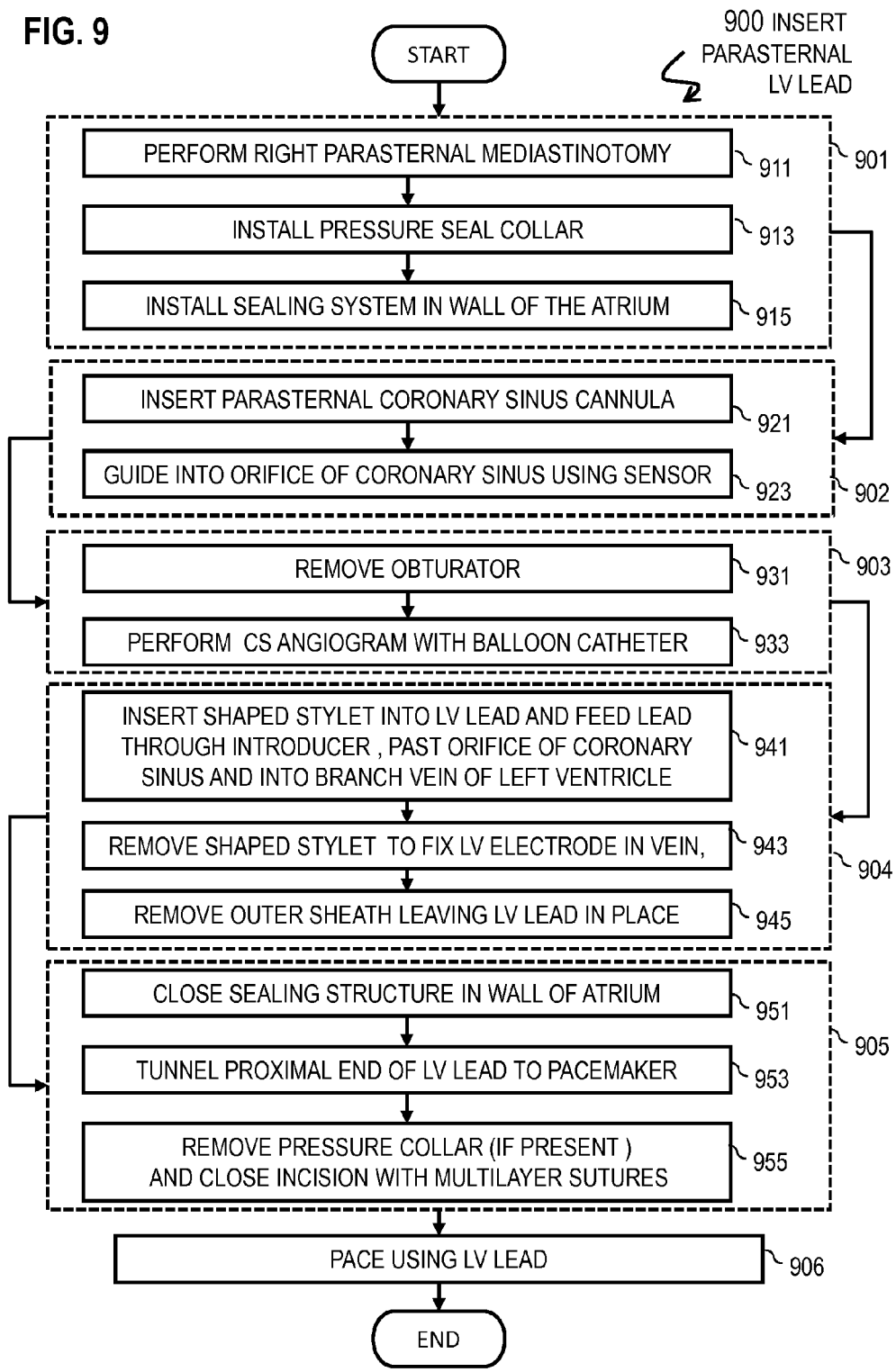

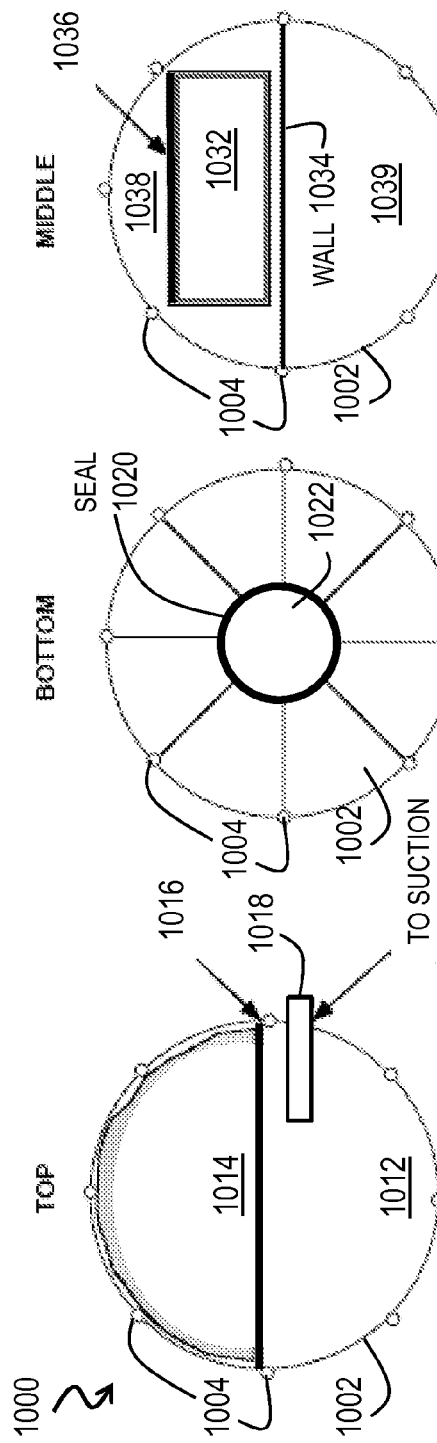

CORONARY SINUS CANNULA WITH LEFT VENTRICLE LEAD AND PRESSURE TENT

CROSS-REFERENCE TO RELATED APPLICATIONS

This application claims benefit of Provisional Appln. 61/223,603, filed Jul. 7, 2009, the entire contents of which are hereby incorporated by reference as if fully set forth herein, under 35 U.S.C. §119(e). This application also claims benefit of Provisional Appln. 61/304,221, filed Feb. 12, 2010, the entire contents of which are hereby incorporated by reference as if fully set forth herein, under 35 U.S.C. §119(e). Furthermore, this application also claims benefit of Provisional Appln. 61/318,682, filed Mar. 29, 2010, the entire contents of which are hereby incorporated by reference as if fully set forth herein, under 35 U.S.C. §119(e).

STATEMENT OF GOVERNMENTAL INTEREST

This invention was made with Government support under Grant No. HL-080152 awarded by the National Institutes of Health. The government has certain rights in the invention.

BACKGROUND

One treatment for heart failure includes biventricular pacing (BiVP), by which electrical signals are introduced at electrodes at two or more locations distributed across both the right ventricle and left ventricle of the heart to induce efficient and regular heart activity. A device that provides for permanent biventricular pacing is a biventricular pacemaker, which can be implanted through catheters without open chest or open heart surgery.

The process of implanting a left ventricle (LV) electrode for a BiVP pacemaker involves introducing a catheter two feet in length into a vein near a shoulder of the patient, and navigating the catheter into the right atrium and thence into an orifice into the coronary sinus. Once the guiding catheter is positioned in the coronary sinus, an angiogram is performed to delineate branch veins. Next, a pacing lead containing one or two conductors and typically 3 mm×65 cm in length is advanced into a branch vein. The tip of the catheter is guided using any X-ray fluoroscopy and an over-the wire technique. Even so, a skilled electrophysiologist with several hours of time available, is unable to successfully place the electrode end of the LV lead in a branch vein about 10 percent of the time. In such cases the procedure is a failure and other means to treat heart failure have to be called upon, including biventricular pacing via an epicardial (open chest) approach.

SUMMARY OF EXAMPLE EMBODIMENTS

Some techniques are provided for placing a BiVP coronary sinus lead for any purpose, including for permanent BiVP or for temporary BiVP, with open chest surgery that is less invasive than open heart surgery. Some techniques are provided for even less invasive parasternal lead insertion. Some techniques are directed to parasternal procedures, in general, without negative room pressure.

In an approach designed by the current inventors, BiVP is desired for a limited time (e.g., about 24 hours) after open heart surgery to help synchronize the heart recovering from ischemic arrest induced during the surgery. In such circumstances, the inside of the heart is already accessible by virtue of normal procedures, such as insertion of a cardioplegia cannula, and a long catheter introduced at the patient's shoulder is both superfluous and unwieldy. During primary open heart surgery, the outside of the left ventricle is also accessible and the left ventricle is mobilized so that a lead with desired electrode can be sewn directly in place. However, during subsequent open-heart surgery (re-operation), adhesions that result from the primary operation introduce complications that advise against mobilizing the left ventricle, and a different means is needed to place the left ventricle lead with its electrode more safely.

According to a first set of embodiments, a lead for a pacing electrode includes a hollow tube of flexible material open at a proximal (device) end and an electrode at a distal (cardiac) end of the hollow tube. An electrical conductor electrically connects the electrode to the proximal end and is positioned within the flexible material. A shaped stylet of rigid material is disposed inside the hollow tube at the distal end and is removable through the open proximal end. The shaped stylet is curved in a first plane to match a curve of a left ventricle portion of coronary sinus and curved in a different second plane to match a curve of a branch vein of the coronary sinus.

According to another set of embodiments, a lead for a pacing electrode includes a hollow tube of flexible material open at a proximal (device) end and an electrode at a distal (cardiac) end of the hollow tube. An electrical conductor electrically connects the electrode to the proximal end and is positioned within the flexible material. The proximal end is configured to be releasably connected physically and electrically to a pacing signal generator.

According to another set of embodiments, a lead for a pacing electrode includes a hollow tube of flexible material open at a proximal (device) end and an electrode at a distal (cardiac) end of the hollow tube. An electrical conductor electrically connects the electrode to the proximal end and is positioned within the flexible material. The distal end is configured to hook into a wall of a branch vein when a rigid stylet is retracted through the open proximal end.

According to another set of embodiments, a lead for a pacing electrode includes a hollow tube of flexible material open at a proximal (device) end and an electrode at a distal (cardiac) end of the hollow tube. An electrical conductor electrically connects the electrode to the proximal end and is positioned within the flexible material. The hollow tube and electrode have a diameter less than an inner diameter of a cardioplegia cannula catheter.

According to another set of embodiments, a kit for a lead for a pacing electrode includes a hollow tube of flexible material open at a proximal (device) end and an electrode at a distal (cardiac) end of the hollow tube. An electrical conductor electrically connects the electrode to the proximal end. A shaped stylet of rigid material is included for insertion and removal through the hollow proximal end to position in the hollow tube at the distal end. The shaped stylet is curved in a first plane to match a curve of a left ventricle portion of coronary sinus and curved in a different second plane to match a curve of a branch vein of the coronary sinus.

According to another set of embodiments, a method for placing a left ventricle pacing electrode includes inserting a cardioplegia cannula catheter through an orifice from a right atrium to a coronary sinus. A distal (cardiac) end of a left ventricle lead that includes a shaped stylet in a hollow tube is fed through the cardioplegia cannula catheter into the coronary sinus and a branch vein of the coronary sinus. The cardioplegia cannula catheter is removed and the shaped stylus is retracted. The left ventricle lead includes the hollow tube made of flexible material and open at a proximal end and an electrode at a distal end of the hollow tube. An electrical conductor electrically connects the electrode to the proximal end and is positioned within the flexible material. The shaped stylet of rigid material is inside the hollow tube at the distal end and is removable through the open proximal end.

According to another set of embodiments, a cannula includes an outer sheath and an obturator. The outer sheath includes a flexible hollow shaft of sufficient length to extend from outside a subject's body through a right parasternal mediastinotomy incision to a coronary sinus orifice in a right atrium of a heart of the subject. The obturator is removeably disposed inside the outer sheath from a proximal (device) end of the hollow shaft. The obturator includes a flexible stem that fits snugly inside the hollow shaft, a malleable core disposed inside the flexible stem, a tapered tip that extends beyond a distal (cardiac) end of the shaft when the obturator is disposed inside the outer sheath, and a sensor for determining properties of the subject in a vicinity of the tapered tip.

According to another set of embodiments, a kit for a cannula includes an outer sheath, a obturator and a lead. The outer sheath includes a flexible hollow shaft of sufficient length to extend from outside a subject's body through a right parasternal mediastinotomy incision to a coronary sinus orifice in a right atrium of a heart of the subject. The obturator is reversibly insertable inside the outer sheath from a device end of the hollow shaft. The obturator comprises a flexible stem that fits snugly inside the hollow shaft, a malleable core disposed inside the flexible stem, a tapered tip that extends beyond a cardiac end of the shaft when the obturator is disposed inside the outer sheath, and a sensor for determining properties of the subject in a vicinity of the tapered tip. The lead is insertable inside the outer sheath from a device end of the hollow shaft. The lead includes a hollow tube of flexible material open at a device end, a first electrode at a cardiac end of the hollow tube, a first electrical conductor that electrically connects the first electrode to the device end and that is positioned within the flexible material, and a shaped stylet of rigid material inside the hollow tube at the cardiac end and removable through the open device end.

According to another set of embodiments, a method for operating a cannula includes shaping a malleable core of an obturator to reach a coronary sinus orifice in a right atrium from an entry point in the right atrium. A cannula is inserted through a right parasternal mediastinotomy incision to a coronary sinus. The cannula comprises an outer sheath and the obturator. The outer sheath includes a flexible hollow shaft. The obturator is removeably disposed inside the outer sheath from a device end of the hollow shaft. The obturator comprises a flexible stem that fits snugly inside the hollow shaft, the malleable core disposed inside the flexible stem, and a tapered tip that extends beyond a cardiac end of the shaft when the obturator is disposed inside the outer sheath. The method further comprises removing the obturator, and feeding a cardiac end of a left ventricle lead that includes a shaped stylet in a hollow tube through the outer sheath into the coronary sinus and a branch vein of the coronary sinus. The method further comprises retracting the shaped stylus; and removing the outer sheath.

According to another set of embodiments, a surgical pressure tent includes a rigid framework circumscribing a volume sufficient to accommodate manipulators to perform a surgery. The tent also includes a sheet of flexible material impervious to airflow and having a surgical opening, with a sealing material along a perimeter of the surgical opening. The tent further includes a pressure hose fitting. The sheet of flexible material is attached to the framework to prevent airflow into the circumscribed volume except through the surgical opening. The sealing material forms a seal against a skin surface of a patient sufficient to withstand pressure differences up to about 10 centimeters of water (cm H2O). The pressure hose fitting is configured to allow the circumscribed volume to be connected to an air pump to establish a target pressure inside the circumscribed volume.

According to another set of embodiments, a method includes using the pressure tent for parasternal insertions.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3A is a block diagram illustrating apparatus for placement of a left ventricle pacing lead, according to an embodiment;

FIG. 3B is a block diagram illustrating an expanded view of a left ventricle pacing lead, according to an embodiment;

FIG. 5 is a flow diagram for a method for pacing a heart with a left ventricle pacing lead, according to an embodiment;

FIG. 6A is a block diagram illustrating a parasternal coronary sinus cannula, according to an embodiment;

FIG. 6B is a block diagram illustrating the tear-away outer sheath with the obturator removed, according to an embodiment;

FIG. 6C is a block diagram illustrating the tear-away outer sheath with a left ventricle pacing lead inserted, according to an embodiment;

FIG. 8A is a diagram illustrating a pressure seal collar, according to an embodiment;

FIG. 8B is a diagram illustrating a modified parasternal coronary sinus cannula, according to an embodiment;

FIG. 8C is a diagram illustrating a self-sealing system deployed at an atrium wall, according to an embodiment;

FIG. 9 is a flow diagram illustrating a method for operating a parasternal coronary sinus cannula to pace a heart with a left ventricle pacing lead, according to an embodiment;

FIG. 10A is a block diagram illustrating a plan view of a top surface of a surgical pressure tent for parasternal insertions, according to an embodiment;

FIG. 10B is a block diagram illustrating a plan view of a bottom surface of a surgical pressure tent for parasternal insertions, according to an embodiment;

FIG. 10C is a block diagram illustrating a plan view of a middle section of a surgical pressure tent for parasternal insertions, according to an embodiment;

FIG. 10D is a block diagram illustrating an elevation view of a side of a surgical pressure tent for parasternal insertions, according to an embodiment;

FIG. 10E is a block diagram illustrating an elevation view of a front of a surgical pressure tent for parasternal insertions, according to an embodiment;

FIG. 10F is a block diagram illustrating an elevation view of a side of a collapsed surgical pressure tent, according to an embodiment.

DETAILED DESCRIPTION

Figure 1A:
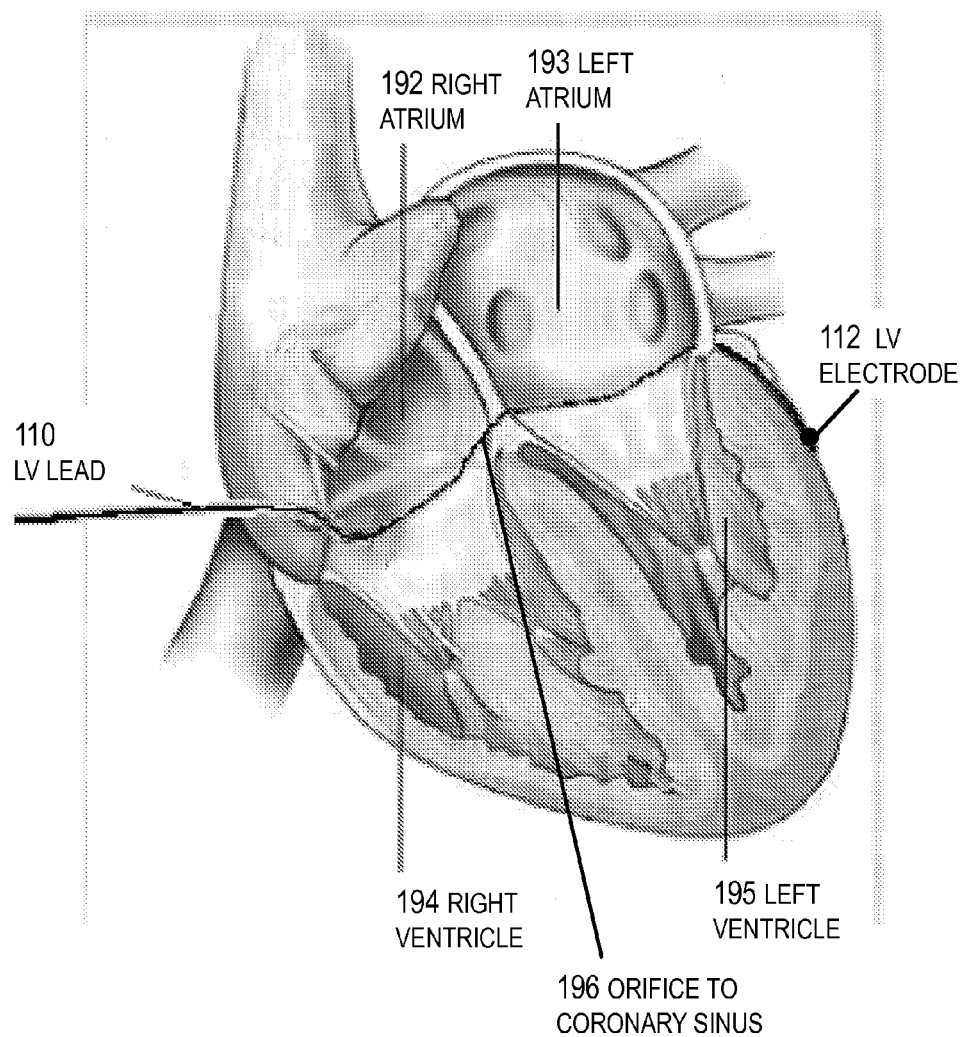
FIG. 1A is diagram that illustrates placement of a left ventricle pacing lead in a cutaway anterior view of a human heart, according to an embodiment.

A method and apparatus are described for operating a coronary sinus cannula, e.g., to place a left ventricle lead for BiVP. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of placement of left ventricle leads for permanent BiVP. However, the invention is not limited to this context. In other embodiments, the apparatus or methods are used for temporary BiVP, or for other purposes. For example, the cannula is useful for all lead insertions or when a transvenous approach is not possible or practical or is not recommended. Lead insertions include lead insertions for right atrium (RA) or right ventricle (RV) leads for pacemakers or implantable cardioverter defibrillator (ICD). A standard transvenous approach is not possible or practical or is not recommended for thrombosis, or obstruction of the superior vena cava. Examples include tumor-induced mechanical obstruction. Caval thrombosis can be related to infection on chronically implanted pacemaker or ICD leads. Caval thrombosis also occurs spontaneously with pacemaker or ICD leads, due to local inflammation or a severe intrinsic clotting response. Some patients also have a spontaneous tendency to form strictures in the venous system, with or without the presence of foreign material. Certain forms of congenital venous abnormalities prevent a direct endocardial approach to the heart. Some surgical operations deliberately obstruct the vena cava with ties and/or division.

Overview

A new technique is described herein to insert leads designed and approved for permanent pacing within the venous system of the heart, e.g., the coronary sinus and its branches. The leads are guided into the coronary sinus via a coronary sinus cannula that is used with open heart surgery (cardioplegia cannula) or a modified cannula that can be used without open heart surgery (parasternal coronary sinus cannula). The distal end (the end that is to be disposed closest to the heart, called the cardiac end hereinafter) of the cannula is guided into position through a right atrium puncture. The lead includes a rigid shaped stylet that conforms to the expected curves of the coronary sinus and branch vein. The cardiac end of the lead is guided to an appropriate venous branch, and the proximal end (the end that is to be attached to an external device, called the device end hereinafter) of the lead is attached to an appropriate pacemaker.

In some embodiments the coronary sinus cannula is used during open heart (open chest) surgery. In some embodiments, a parasternal coronary sinus cannula is included that is used without open chest surgery; but guided into position using echocardiography, pacing thresholds or other methods. An obturator (an object used to obstruct a hole) within the cannula is replaced by the lead, such as a left ventricle lead with the shaped rigid stylet. An outer sheath of the parasternal coronary sinus cannula is removed; and the device end is tunneled to the appropriated pacemaker.

Left Ventricle Lead

In an illustrated embodiment, the left ventricle lead used for this purpose is flexible, bipolar in design with tip and ring electrodes 1-3 centimeters (cm, 1 cm=$10^{-2}$ meters) apart. The length of the lead is about 25 centimeters, short enough to conveniently pass through the cannula and long enough to be attached or tunneled to a permanent or temporary pacemaker. The lead is iso-diametric and small enough to pass easily through an outer sheath of the cannula, allowing the cannula to be withdrawn over it, leaving the lead properly positioned in the coronary sinus. The lead has a central channel that contains a stylet that can be withdrawn. The shape of the stylet conforms to the anticipated curvature of the posterior left ventricle and coronary veins. That is, a compound curve around the back of the heart following the curve of the coronary sinus ending in a compound curve to the right of an observer facing the orifice of the coronary sinus. A cardiac tip of the lead is angled slightly to help retain the lead in place. The stylet is removable after lead placement, rendering the lead soft to minimize the chance of ventricular perforation. In some embodiments, the tip contains physical emitters to assist in lead positioning—these might include a bright light (fiber optic) source, an ultrasound emitter, an EMF transponder, or other active or passive emitters of energy used for guidance. In some embodiments the stylet is not used; and, after placement in the coronary sinus, conventional venography, fluoroscopy, and over-the-wire insertion techniques are used to guide the lead tip to a location appropriate for permanent pacing, as judged by mechanical stability, absence of phrenic nerve pacing, and appropriate sensing, impedance and pacing threshold.

Thus in some embodiments, a lead for a pacing electrode includes one (unipolar) or two (bipolar) coiled conductors within a tube of flexible insulating material open at a device end. One or two contact electrodes are at a cardiac end of the lead. The coiled conductors electrically connect the electrode (s) to the device end and are positioned within the flexible material. A relatively rigid, removable wire stylet is inserted inside the hollow channel from the device end throughout the length of the lead. The shaped stylet is curved in a first plane to match a curve of a left ventricle portion of coronary sinus and curved in a different second plane to match a curve of a branch vein of the coronary sinus. In some embodiments, the device end is configured to be releasably connected physically and electrically to a pacing signal generator. In some embodiments, the cardiac end is configured to hook into a wall of a branch vein when a rigid stylet is retracted through the open device end. In some embodiments, the hollow tube and electrode have a diameter less than an inner diameter of a outer sheath for a coronary sinus cannula, described below. Recent experience has shown the value of these leads.

FIG. 1A is diagram that illustrates placement of left ventricle pacing lead 110 in a cutaway anterior view 190*a* of a human heart, according to an embodiment. The right atrium 192, left atrium 193, right ventricle 194 and left ventricle 195 are depicted. After placement, the left ventricle (LV) lead 110 extends from outside the heart into the right atrium 192 through an orifice 196 to a coronary sinus that rings the outside of the left ventricle, through a portion of the coronary sinus outside the heart and down a branch vein. At a cardiac end of the lead is the LV electrode 112, such as a single electrode or, preferably, a bi-polar electrode that comprises two separate electrodes that are oppositely charged during operation.

Figure 1B:
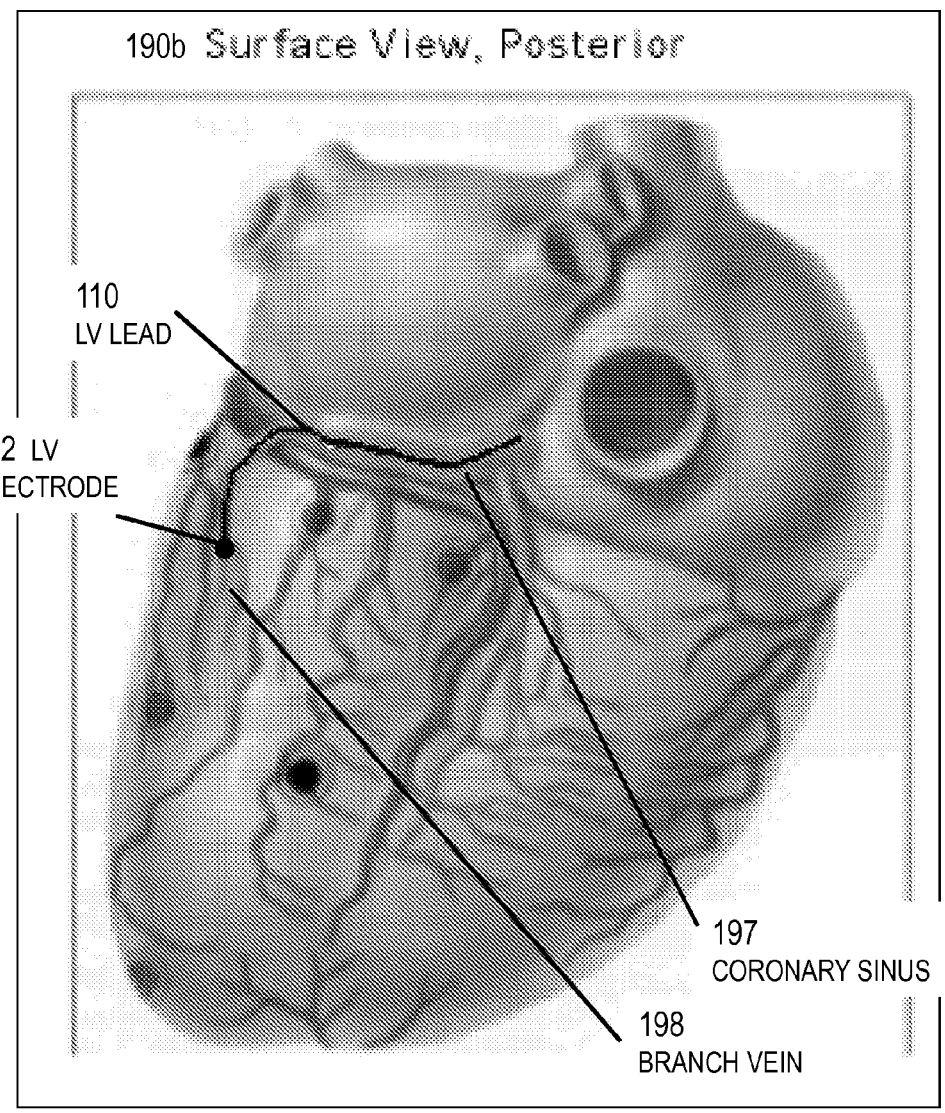
FIG. 1B is diagram that illustrates placement of a left ventricle pacing lead in a surface posterior view of a human heart, according to an embodiment.

FIG. 1B is diagram that illustrates placement of the left ventricle pacing lead 110 in a surface posterior view 190*b* of a human heart, according to an embodiment. The coronary sinus 197 and branch vein 198 are depicted. As shown, the lead 110 extends along a portion of the coronary sinus 197 and into the branch vein 198, where the LV electrode 112 is positioned.

During open heart (open chest) surgery, a cardioplegia cannula, which is a catheter with multiple access ports and stiffened by a removable rigid stylet, enters the heart through a stab wound in the right atrium and is advanced to the orifice 196 of the coronary sinus 197 and then a short way, about one or two centimeters, into the coronary sinus 197. A pursestring suture is sewn around the catheter to prevent fluid loss. The rigid stylet is removed, and there is room between the cannula and the wall of the coronary sinus to allow normal flow of blood from the coronary sinus back into the right atrium. According to various embodiments, the catheter of the cardioplegia cannula provides a path that is used to pass the LV lead 110 into the coronary sinus during placement of the LV lead 110.

Left Ventricle Stylet

According to one embodiment, the LV lead itself is stiffened with a shaped stylet of rigid material. The shaped stylet is curved in a first plane to match a curve of a left ventricle portion of the coronary sinus and curved in a different second plane to match a curve of a branch vein of the coronary sinus. The two curves meet at an angled portion that matches the angle between the branch vein and the coronary sinus in the heart.

Figure 2A:
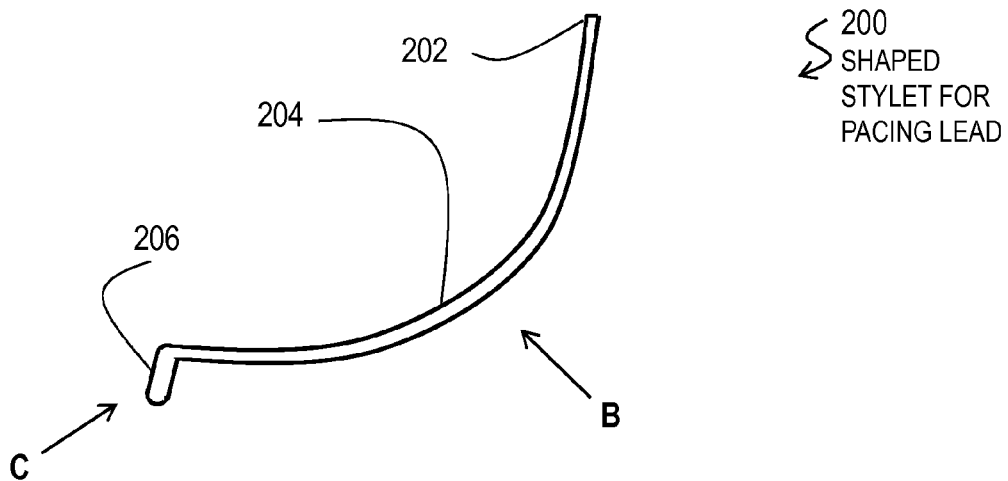
FIG. 2A is a plan view of a rigid shaped stylet for a left ventricle pacing lead, according to an embodiment.
Figure 2B:
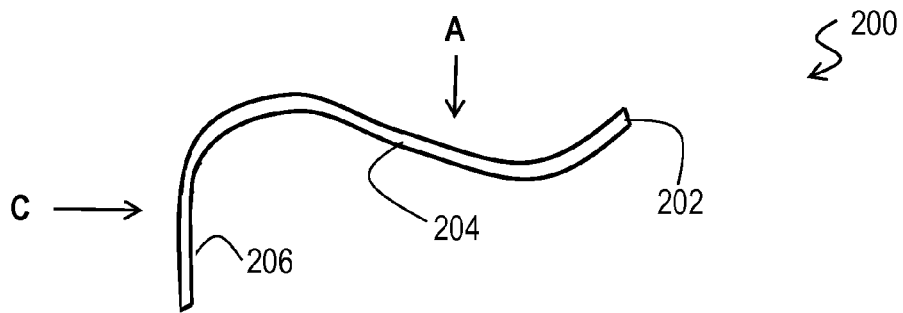
FIG. 2B is a elevation view of a rigid shaped stylet for a left ventricle pacing lead, according to an embodiment.
Figure 2C:
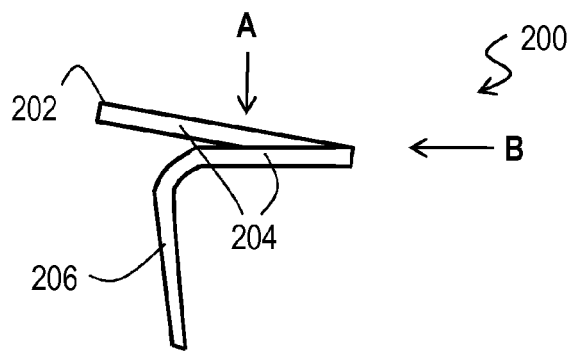
FIG. 2C is a perpendicular elevation view of a rigid shaped stylet for a left ventricle pacing lead, according to an embodiment.

FIG. 2A is a plan view of a rigid shaped stylet 200 for a left ventricle pacing lead, according to an embodiment. Looking from the top when placed in the heart, the shaped stylet 200 includes a device end 202 a first curved portion 204 and a second curved portion 206. The first curved portion 204 is in a first plane of the plan view and approximates the curve of a portion of the coronary sinus between the orifice 196 into the right atrium and a targeted branch vein. The second curved portion 206 is in a second plane approximately perpendicular to the first plane and approximates the curve of a branch vein feeding into the coronary sinus. Two directions of elevation views indicated by arrow B and arrow C correspond to views depicted in FIG. 2B and FIG. 2C, respectively. FIG. 2B is an elevation view of the rigid shaped stylet 200 for a left ventricle pacing lead, according to an embodiment. This elevation view is approximately perpendicular to the plane of curvature of portion 206. Two directions of views indicated by arrow A and arrow C correspond to views depicted in FIG. 2A and FIG. 2C, respectively. FIG. 2C is a perpendicular elevation view of the rigid shaped stylet 200 for a left ventricle pacing lead, according to an embodiment. This elevation view is approximately perpendicular to the elevation view of FIG. 2B. Two directions of views indicated by arrow A and arrow B correspond to views depicted in FIG. 2A and FIG. 2B, respectively. No such shaped rigid stylet is currently used in heart catheters or pacing leads.

FIG. 3A is a block diagram illustrating apparatus 300 for placement of a left ventricle pacing lead, according to an embodiment. The heart 390 is represented schematically as an oval and includes an orifice 392 between a right atrium and a coronary sinus, the coronary sinus 394 and branch veins 396. The coronary sinus 394 and branch veins 396 in a posterior portion of the heart are represented by dashed borders. Although the heart 390 is depicted for reference, the heart 390 is not part of apparatus 300.

The apparatus 300 includes the catheter 310 of the cardioplegia cannula with the straight rigid stylet removed and a LV lead 320 inserted. In some embodiments, the catheter 310 includes a port 311 for fluid profusion or removal during cardiac surgery. Leakage is prevented by a purse-string suture 312 circling the catheter 310. The LV lead 320 includes a device end 322 and a cardiac end 324 with one or more electrodes (not shown), with the rigid shaped stylet 200 in place in the cardiac end. The rigid shaped stylet 200 is used by the surgeon to advance the cardiac end 324 of the LV lead 320 from the orifice 392 through the coronary sinus 394 and into one of the branch veins 396. The entire length of LV lead 320 is smaller in diameter than the inside diameter of the cannula catheter 310, so that the cardiac end 324 can be fed through the catheter 310 and so that the catheter 310 can be removed past the device end 322, while the LV lead 320 stays in place.

In some embodiments, the cannula 310 includes one or more sensors or transmitters to help guide the cardiac end of the cannula into the coronary sinus orifice 392. In such embodiments, the sensors or transmitters are in communication with a guidance system 380, such as a general purpose computer, comprising one or more chip sets, programmed to perform one or more guidance functions. A chip set is described in more detail below with reference to FIG. 10.

FIG. 3B is a block diagram illustrating an expanded view of a left ventricle pacing lead 320, according to an embodiment. The LV pacing lead 320 is a hollow tube of flexible material 326 made hollow by a channel 328 open at least at the device end 322. The cardiac end 324 includes two separate ring electrodes 342*a* and 342*b* collectively called LV electrode 342 and forming a bipolar electrode 342. In some embodiments, electrode 342*b* is a tip electrode disposed at the tip of cardiac end 324 rather than a ring apart from the tip, as depicted in FIG. 3B. The electrode 342*a* is electrically connected to device end 322 by conductor 344*a* in the flexible material 326. Similarly, the electrode 342*b* is electrically connected to device end 322 by a separate conductor 344*b* in the flexible material 326. The two conductors are electrically isolated, e.g., by electrical insulation properties of the flexible material 326, or by additional insulated coatings. In some embodiments, a unipole electrode is disposed at the cardiac end 324 and a single conductor electrically connects the unipole electrode to the device end.

Figure 3C:
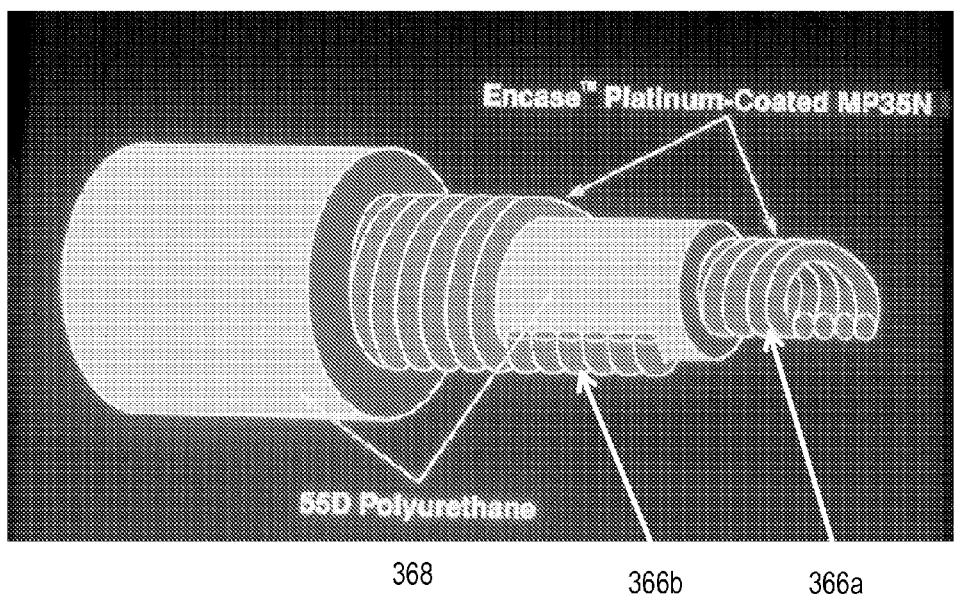
FIG. 3C is a block diagram illustrating coiled conductors in a pacing lead, according to an embodiment.

FIG. 3C is a block diagram illustrating coiled conductors in a pacing lead, according to an embodiment. In this embodiment the flexible material 368 is 55D Polyurethane separating an inner coiled conductor 366a for one electrode from an outer coiled conductor 366b for a second electrode. In this embodiment, the conductors are formed in coils to allow flexion and expansion and reduce the risk of fracture during and after placement in the subject's heart.

In some embodiments, the device end 322 is configured to be releasably connected physically and electrically to a pacing signal generator, without exceeding the inner diameter of the cannula catheter. In the illustrated embodiment, this property is accomplished by a protruding electrically conducting peg connected to each conductor, e.g., peg 346a electrically connected to conductor 344a and peg 346b electrically connected to conductor 344b, both pegs (collectively referenced as pegs 346) attached to the flexible material 326. Although the pegs 346 are shown spaced on opposite sides of the device face of the flexible tube, in some embodiments, the pegs are spaced differently to make clear which peg is associated with which of the spaced electrodes 342. In some embodiments, other physical or electrical connections are made, such as ring contacts along the outside of the tube or threaded tube end, such as a male thread, or both.

The entire length of LV lead 320 has a diameter 350 less than the diameter of the inside of the cannula catheter. The inner diameter of the cannula is about 0.25 cm; the outer diameter of the lead is about 0.20 cm. The LV lead 320 has a length 352 sufficient to reach from the branch vein 396 through the right atrium and outside the skin of the patient whose heart is to be paced, about 25-50 cm in some embodiments. The electrodes 342 are spaced apart by a distance 354 of about one or two centimeters. The channel 328 allows the rigid shaped stylet 200 to be inserted into the LV lead up to the cardiac end and to be retracted through the device end after the LV lead 320 is in place. The flexible tube adapts to the shape of the rigid shaped stylet when the stylet is positioned in the channel 328. The LV lead 320 is depicted in FIG. 3B without the rigid shaped stylet 200 inserted in the channel 328. In some embodiments, the stylet is replaced with a flexible over-the-wire type guidewire that passes out through an opening at 332 and is advanced under fluoroscopic guidance to a desired CS branch. The lead is then advanced forward over this guidewire. Once the lead is positioned and tested, the guidewire is withdrawn.

In the illustrated embodiment, the cardiac end 324 of the LV lead 320 includes a protuberance 330 that is salient when the rigid shaped stylet 200 is retracted from the cardiac end 324. This protuberance 330 serves as a wedge or hook to lodge the cardiac end 324 in the branch vein until the lead is extracted. Thus, the cardiac end 324 is configured to hook into a wall of a branch vein when a rigid stylet 200 is retracted through the open device end 322.

In the illustrated embodiment, the cardiac end 324 of the LV lead includes a guidance component 332 used to determine the position of the tip relative to the anatomy of the heart during insertion of the LV lead 320 through the coronary sinus 394 and branch vein 396. Any guidance component known in the art may be used, such as a bright light (fiber optic) source, an ultrasound emitter, an electromagnetic field (EMF) transponder, or other active or passive emitters of energy. In various embodiments, the component 332 is a probe for a guidance system that is not within the LV lead but is within the obturator used to insert the cannula. Component 332 in such embodiments is at least one of an X-ray fluoroscope guidance system, an echocardiography guidance system, an electrical guidance system, a thermography guidance system, or a radio frequency identification (RFID) guidance system, among others. In some embodiments, guidance component 332 is omitted, and the surgeon works entirely by feel and orientation.

Figure 4A:
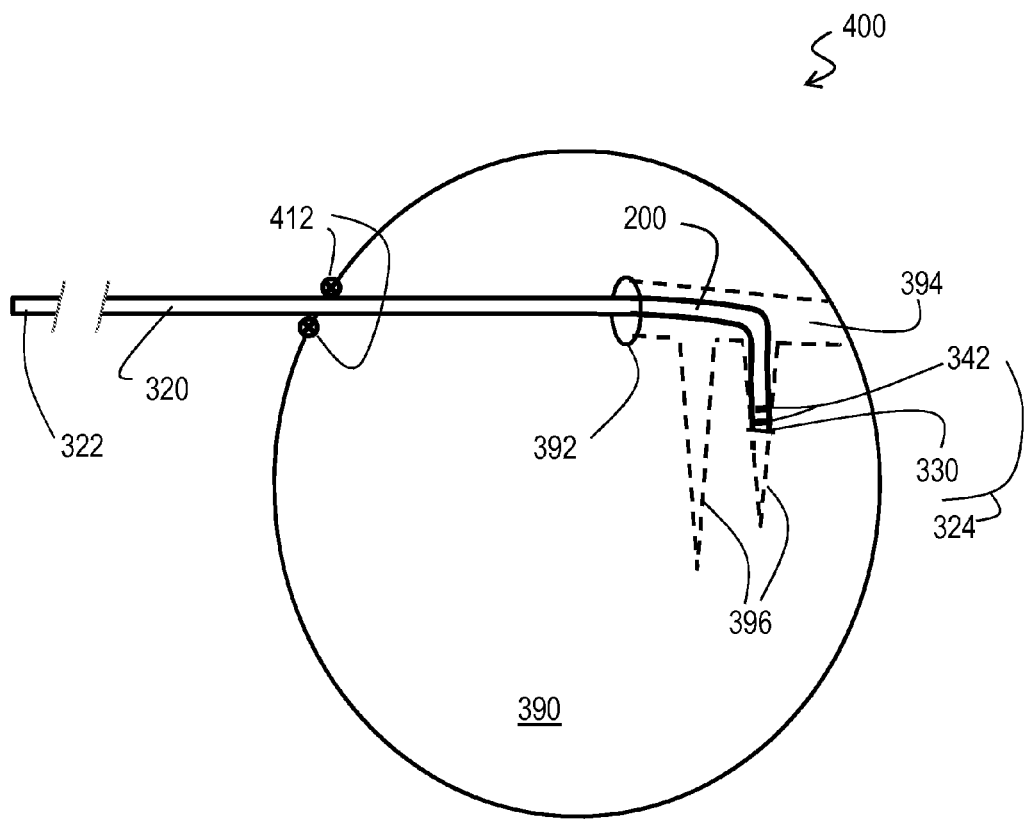
FIG. 4A is a block diagram illustrating placement of a left ventricle pacing lead, according to an embodiment.

FIG. 4A is a block diagram illustrating placement of a left ventricle pacing lead 320, according to an embodiment. The catheter 310 of the cannula has been removed and the rigid shaped stylet 200 has been retracted through the opening of the hollow tube at the device end 322. A tightened pursestring suture 412 prevents leakage after removal of the cannula catheter 310. As can be seen, the bipolar electrode 342 at the cardiac end 324 of the LV lead 320 is in place in the branch vein 396, held in place by the protuberance 330 that has expanded upon retraction of the shaped stylet 200. The device end 322 is accessible for connection to a permanent or temporary pacing signal source or generator in a pacing system.

Figure 4B:
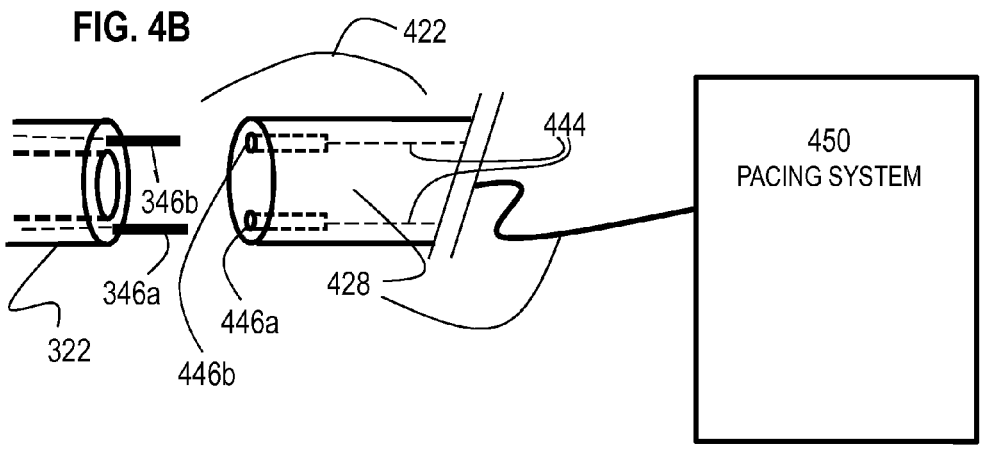
FIG. 4B is a block diagram illustrating an expanded view of a connection of a left ventricle pacing lead to a pacing system, according to an embodiment.

FIG. 4B is a block diagram illustrating an expanded view of a connection of a left ventricle pacing lead 320 to a pacing system 450, according to an embodiment. The pacing system 450 includes one or more pacing signal generators (not shown) configured to generate pacing signals for one or more leads. It is assumed for purposes of illustration that cable 428 is connected to a pacing signal generator (not shown) for producing a pacing signal for bipolar LV electrode 342. The end 422 of cable 428 is configured to be releasably or permanently connected physically and electrically to the device end 322 of the LV lead 320.

In the illustrated embodiment, end 422 of the cable 428 includes two sockets, socket 446a and socket 446b, collectively called socket 446, electrically connected by insulated conductors 444 in cable 428 to the pacing system 450. Peg 346a and peg 346b are configured to fit snugly into socket 446a and socket 446b, respectively, to make electrical and mechanical connection to cable 428.

The heart 390 can be paced by signals delivered from pacing system 450 to electrodes 342 via cable 428 and LV lead 320. Upon completion of temporary pacing, the lead 320 is extracted from the heart 390, and the opening closed by further tightening purse-string suture 412. Thus temporary BiVP is permitted even after re-operation. For permanent pacing, the lead is not removed but is secured in position by the atrial sealing component (either purse string suture, or a self-sealing system described below). An extender is attached to the device end of the lead and tunneled subcutaneously to a generator pocket, usually in the left subclavian region.

Open Chest Operation

FIG. 5 is a flow diagram for a method 500 for pacing a heart with a left ventricle pacing lead, according to an embodiment. Although steps in FIG. 5, and subsequent flowcharts, are show in a particular order for purposes of illustration, in other embodiments, one or more steps may be performed in a different order or overlapping in time, in series or in parallel, or one or more steps may be omitted or added, or changed in some combination of ways.

In step 501, a purse-string suture (e.g., 312) is sewn at the point where the cardioplegia cannula is to be inserted to prevent fluid leakage from the heart after insertion. In some embodiments step 501 is performed after opening a patient's chest as part of open heart surgery, e.g. bypass surgery.

In step 503 the cardioplegia cannula stiffened by the rigid straight stylet perforates a blood vessel leading to the right atrium and is advanced into the right atrium. In step 505, the surgeon uses the cardioplegia cannula stiffened by the rigid straight stylet to feel for the orifice 392 to the coronary sinus 394, and then advance the cardioplegia cannula stiffened by the rigid straight stylet a centimeter or so into the coronary sinus 394. This procedure is effective in introducing the cannula into the coronary sinus 99% of the time and thus suffers failure only about 1% of the time. This is a small failure rate compared to the 10% failure rate suffered in placing a LV lead for permanent BiVP using the standard long steerable catheter introduced near the patient's shoulder. The rigid straight stylet is then removed from the cannula, during step 505, leaving the cannula catheter 310 in place.

In step 507, the cardioplegia cannula catheter (e.g., catheter 310) is used according to accepted procedures for cardiac surgery, e.g., to inflate a balloon, introduce and suction fluids to induce ischemic arrest of heart activity, sustain the heart during ischemic arrest, perform any open heart surgical procedures, and re-profuse fluids to terminate ischemic arrest. In embodiments in which the cardioplegia cannula is used only to place permanent LV leads for permanent BiVP, step 507 is omitted.

In step 509, the rigid shaped stylet 200 is inserted into the LV lead 320 through the open end of the channel 328 and moved to the cardiac end 324 of the LV lead 320. The shaped lead is then fed through the cardioplegia cannula catheter, cardiac end first, past orifice 392, into coronary sinus 394 and down into a branch vein 396 in the epicardial surface of the left ventricle. In some embodiments, the guidance component 332 at the cardiac end 324 is used with a corresponding guidance system (not shown) to assist the surgeon in feeding the cardiac end into the appropriate branch vein during step 509.

In step 511, the catheter 310 of the cardioplegia cannula is removed, leaving the LV lead 320 in place, by sliding the catheter 310 past the device end 322 of the LV lead 320. Such removal is made possible by a LV lead 320 with a diameter everywhere less than an inner diameter of the catheter 310, such as a constant diameter lead 320, also called an isodiametric lead. This is also permitted by a device end 322 that is removeably connected to the pacing system 450, so that the pacing system 450 does not block the removal of the catheter 310.

In step 513, the rigid shaped stylet 200 is retracted through the open end of channel 328 at the device end 322 of the LV lead 320. The removal of the shaped stylet 200 from the cardiac end 324, allows the protuberance 330 to engage the walls of the branch vein 396. This fixes the LV electrode 342 in place in the branch vein 396. The purse-string suture 312 is tightened to suture 412 to prevent fluid leakage from the heart.

In step 515, the device end of the LV lead is electrically and physically connected to the pacing system 450, e.g. to the end 422 of cable 428 connected to a LV pacing signal generator (not shown) of the pacing system 450.

In step 517, the heart 390 is paced using the pacing system 450 and the LV lead 320, as well as other leads placed in the right atrium and right ventricle (not shown) as is well known in the art. For temporary pacing post surgery, especially post re-operation, step 517 is performed for a limited time, e.g., for 24 hours. For permanent BiVP, step 517 continues for a much longer time (e.g., months and years).

In step 519, the LV lead is retracted by pulling on the device end 322 of the LV lead, causing the protuberance 330 to disengage from the wall of the branch vein. The LV lead 320 is pulled out of the heart 390 and out of the chest of the patient. The purse-string suture is then tightened to close a flap and prevent fluid leakage from the heart. In embodiments for permanent BiVP, step 519 is omitted.

Thus techniques are provided for placement of a left ventricle lead for permanent or temporary BiVP and for post primary and re-operative cardiac surgery.

Parasternal Operation

In some embodiments, a specially designed parasternal coronary sinus cannula is inserted into the heart, without open heart surgery, through an opening in the patient's anterior chest resulting from a parasternal medial sternotomy, such as a right parasternal mediastinotomy (RPMS). As described in more detail below, the parasternal cannula includes an obturator that perforates the blood vessel into the heart and is advanced into the orifice of the coronary sinus, but a balloon need not be deployed, fluids need not be pumped in and ischemic arrest is not induced, as occurs for open heart and bypass surgery. In some embodiments a balloon catheter is inserted through the cannula into the coronary sinus, and an occlusive balloon is inflated for a coronary sinus angiogram, but ischemic arrest is not induced. Instead, the obturator and balloon catheter are removed and the LV lead 320 (with shaped stylet 200 or commercially available guidewire) is inserted through the catheter of the cannula still in place in the orifice to the coronary sinus, and the lead is advanced into place so that the cardiac end is lodged in a selected branch vein.

The advantages of this approach are many, including: (1) minimally invasive; (2) faster than any known technique; (3) higher success rate than any known technique; (4) applicable in presence of pericardial adhesions; (5) adaptable to local anesthesia; and (6) performed in supine position which minimizes physiologic compromise of lateral thoracotomy.

FIG. 6A is a block diagram illustrating a parasternal coronary sinus cannula 600, according to an embodiment. The illustrated cannula 600 includes a tear-away outer sheath 610, outlined in dashed lines, and an obturator 620. The obturator of the illustrated embodiment includes a stem 622, a malleable core 624, a tapered tip, such as tapered soft plastic tip 626 and a sensor suite 630 with two sensor wires 632. The obturator 620 and outer sheath 610 are flexible so as to bend into an appropriate shape for a particular use and retain that shape, by virtue of the malleable core 624. In some embodiments, the malleable core and flexible stem and hollow shaft are shaped in a curve suited to extend through the right parasternal mediastinotomy incision to the coronary sinus orifice of a subject. For purposes of illustration the obturator 620 and outer sheath 610 are shown in a linear, un-bent configuration; and the outer sheath 610 is rendered with dashed lines.

The outer sheath, such as tear-away outer sheath 610, includes a flexible hollow shaft 614 of sufficient length, about 25 cm) to extend from outside a subject's body through a right parasternal mediastinotomy incision to a coronary sinus orifice in a right atrium of a heart of the subject. In some embodiments with a LV lead of small enough outer diameter to fit entirely within this hollow shaft, any flexible outer sheath or introducer that can be retracted from the incision may serve this function. In some embodiments, an LV lead has a larger diameter connecter on its device end for connecting to a pacemaker, and a tear-away outer sheath is desirable. Tear-away outer sheaths or tear-away introducers are known, such as a tear-away sheath introducer kit from REMINGTON MEDICAL, INC.™ of Alpharetta, Ga., USA, or the introducer sheath from W. L. GORE & ASSOCIATES, INC.™ of Newark, Del. Such known sheaths would be chosen to include a flexible shaft that can assume an appropriate shape.

The obturator stem 622 is made of flexible material that can be shaped to define the bent shape of the cannula. The stem 622 fits snugly inside the hollow shaft of the outer sheath 610 to block fluid flow through the hollow shaft. Inside the flexible stem 622 is a malleable core 624 made of a material, such as a metal wire, that can be shaped and hold a given shape. At a cardiac end of the flexible stem 622 is a tapered tip, e.g., tip 626, used to puncture one or more tissue surfaces or slide into orifices as the cannula is inserted into a subject's body. In an illustrated embodiment, the tapered tip 626 is made of a soft plastic.

The obturator 620 is removeably disposed inside the outer sheath, such as tear-away outer sheath 610, from a device end of the hollow shaft. The tapered tip, such as soft plastic tip 626, extends beyond a cardiac end of the hollow shaft when the obturator 620 is disposed inside the outer sheath, such as tear-away outer sheath 610.

In the illustrated embodiment, the obturator 620 include sensor suite 630 of one or more sensors or transmitters to measure the physical properties inside the subject in a vicinity of the tip. For example, in various embodiments the sensor suite 630 includes one or more sensors of a sensor group including a temperature sensor, an ultrasound sensor, a pressure sensor, an oxygen sensor, and a flow velocity sensor. Any sensors known in the art and small enough to fit inside the obturator 620 may be used. For example, in various embodiments the sensor suite includes one or more of an intracardiac echocardiography transducer (e.g., on an Acunav diagnostic ultrasound catheter from ACUSON CORP.™ of Mountain View, Calif.), a micromanometer pressure sensor (e.g., on a Mikro-Tip catheter from MILLAR INSTRUMENTS, INC.™ of Houston, Tex.), a thermistor (e.g., from ATC SEMITEC LTD™ of Northwich, United Kingdom), an oximetry sensor (e.g., from oximetry catheter of EDWARDS LIFESCIENCES CORPORATION™ of Irvine Calif.), and a flow velocity sensor (e.g., on a catheter from MILLAR INSTRUMENTS, INC.™ of Houston, Tex.) The measurements are used to locate the orifice of the coronary sinus through which blood flows with potentially detectably different values of one or more of these properties.

One or more sensor wires 632 traverse the stem 622 from the sensor suite 630 to a device end of the obturator 620 to communicate measurements from the sensor suite 630 to an external processor, such as guidance system 380, described above with reference to FIG. 3A. In some embodiments, one or more wires are included for each sensor or transmitter. In other embodiments, a single wire is shared and the sensors and transmitters communicate with the external processor such as guidance system 380 using one or more packet switching protocols well known in the art of communications. Such packets can be utilized by a chip set, such as chip set 1000 depicted in FIG. 10, disposed in sensor suite 630 and programmed for such a purpose. In some embodiments, wireless data transmission is used and one or more wires 632 are omitted.

In some embodiments, the cannula is inserted based only on tactile feedback to the surgeon, and sensor suite 630 is omitted.

FIG. 6B is a block diagram illustrating the tear-away outer sheath 610 with the obturator removed, according to an embodiment. This is the configuration after the cardiac end of the outer sheath has been positioned in the orifice of the coronary sinus in the right atrium. The tear-away outer sheath 610 includes the flexible hollow shaft 614 and a handle 612, such as a ring, for initiating a separation process to remove the tear-away outer sheath without dislodging an item disposed inside the sheath. A one-way valve at location 616 prevents bleeding out of the cannula after the obturator is removed.

FIG. 6C is a block diagram illustrating the tear-away outer sheath 610 with a left ventricle pacing lead 320 inserted, according to an embodiment. The LV lead 320 includes device end 322 and a stylus 200 disposed inside the cardiac end. This is the configuration after the LV lead is inserted through the sheath 610 into the branch vein of the coronary sinus and before removing the stylus 200 or initiating the separation process to remove the tear-away sheath 610.

Figure 7A:
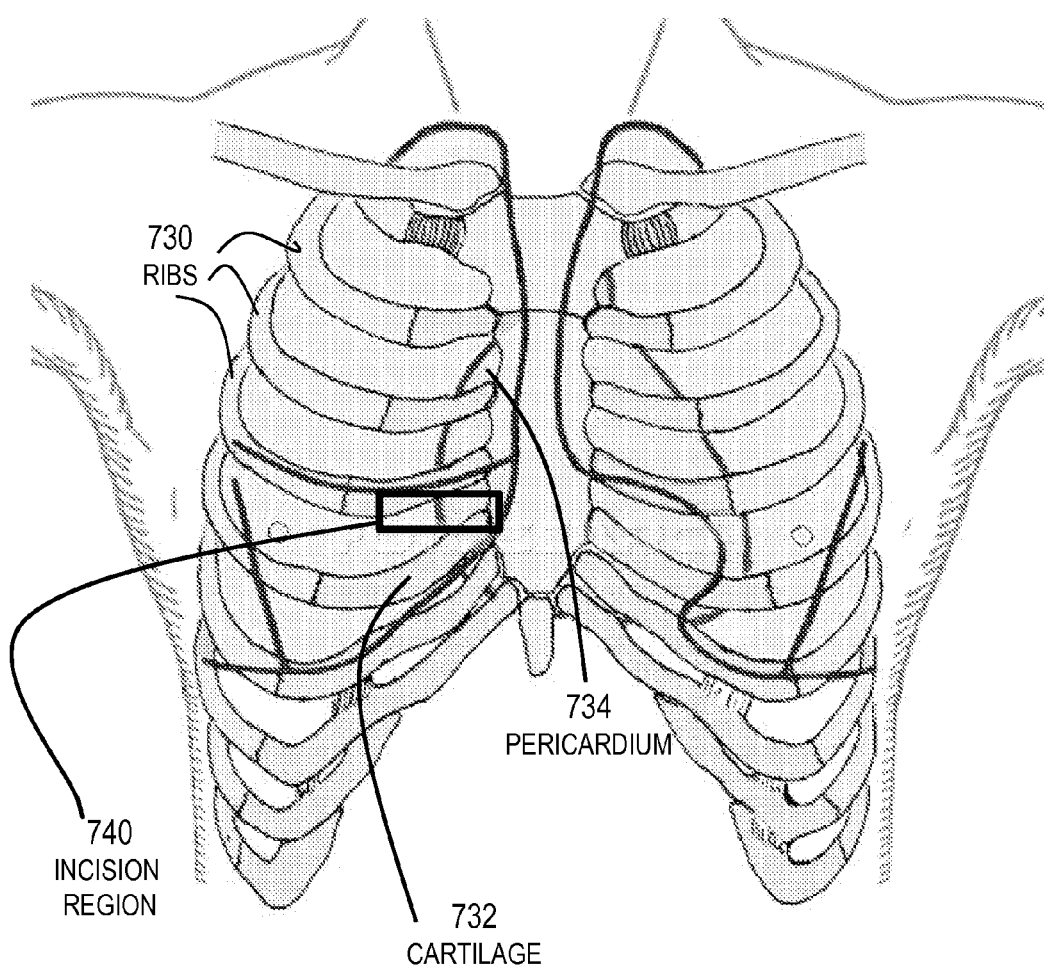
FIG. 7A is a block diagram illustrating a location of a right parasternal mediastinotomy incision, according to an embodiment.

FIG. 7A is a block diagram illustrating a location of a right parasternal mediastinotomy (RPMS) incision, according to an embodiment. The RPMS incision region 740 is depicted relative to ribs 730 and cartilage 732 and pericardium sac 734 of a human subject. RPMS is an established technique originally developed for general thoracic surgery and subsequently used for pacemaker insertion. A transverse incision over the 4th or 5th costal cartilage is fashioned, depending on pre-surgery planning RPMS can be done through any cartilage abutting the sternum, and the decision about which to use would be based on the underlying anatomy. In general, the incision should be made as close as possible to the atrial appendage, and the 4-5 interspace is most likely to be the best. However, the location might change as a result of congenital heart disease or prior surgery, so the surgical team would locate the appendage by trans-thoracic echocardiography or x-ray contrast, magnetic resonance imaging (MRI) or nuclear angiography before beginning the procedure. In some patients, the appendage will have been obliterated, and the lateral wall of the atrium itself will be the best target. Furthermore, anatomic variants might require a mirror image of the surgery described herein, e.g., for situs inversus. Such variants are rare in the general population, but not in the population of patients undergoing surgery for congenital heart disease. The underlying cartilage is resected, and the internal mammary artery and vein (not shown) are divided, if necessary. This provides access to the mediastinal pericardium which is incised to enter the pericardial lumen and expose an appendage of the right atrium of a heart of the subject. RPMS is generally performed with the subject, such as a human patient, under general anesthesia because of the pain of the incision. RPMS is also generally performed with endotracheal intubation and positive pressure ventilation to prevent collapse of the lung when the pleural space is entered. The number of candidates for this procedure is estimated at 90,000 annually, in the U.S.; and technical obstacles to RPSM are rated as substantial, but with potential benefits to many other areas of surgery.

Figure 7B:
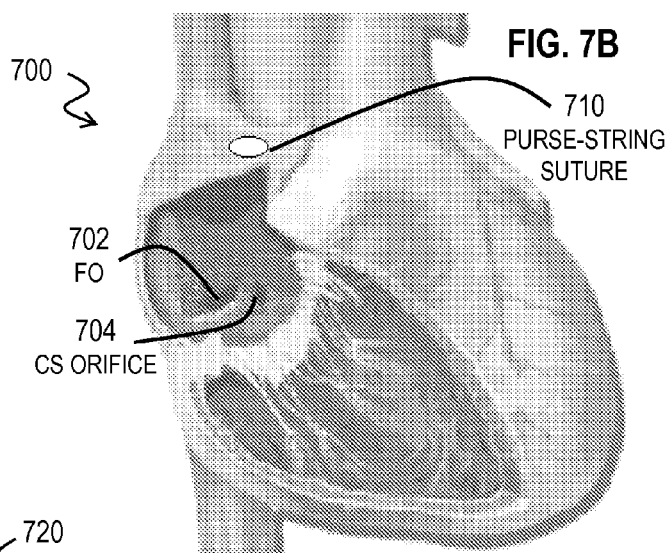
FIG. 7B is a diagram illustrating the location of an entry point in a right atrium and the coronary sinus orifice in a heart of a subject, according to an embodiment.

FIG. 7B is a diagram 700 illustrating the location of an entry point in a wall of a right atrium and the coronary sinus orifice in a heart of a subject, according to an embodiment. The coronary sinus orifice 704 is in a wall of a right atrium close to a foramen ovale (FO) 702. A purse-string suture 710 circuits the entry point in the illustrated embodiment. Placement of the purse-string suture involves general anesthesia for the subject. In some embodiments, a self-sealing system is deposited at the entry point instead of the purse-string suture 710, as described in more detail below with reference to FIG. 8B and FIG. 8C. The use of a self-sealing system enables use of local anesthesia instead of general anesthesia in some embodiments.

Figure 7C:
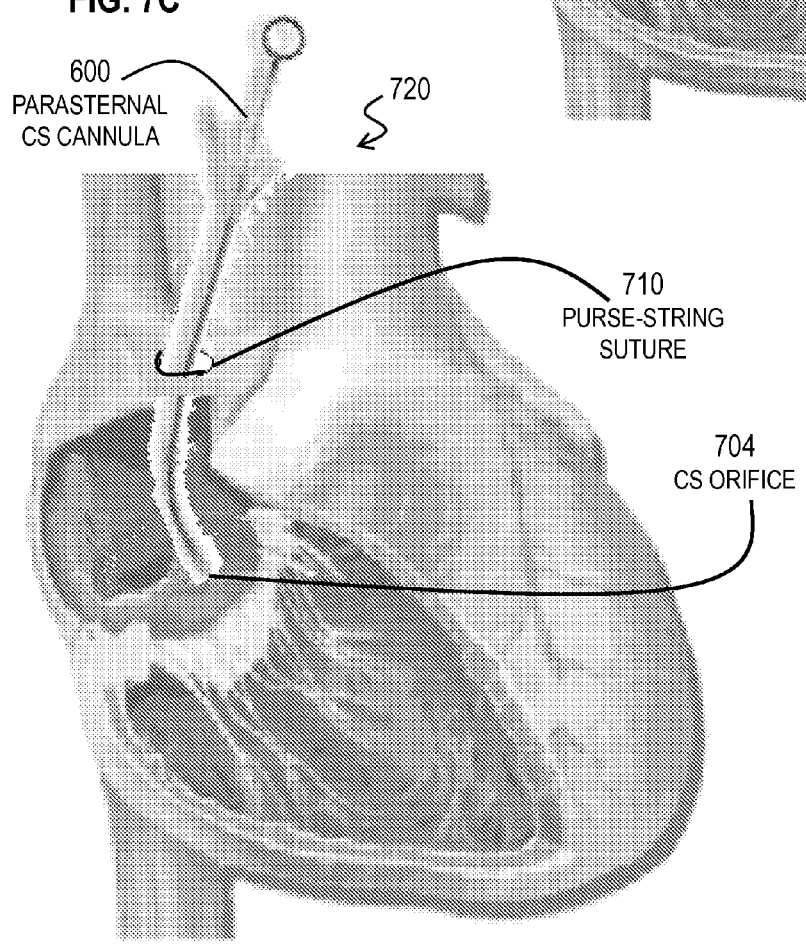
FIG. 7C is a diagram illustrating the coronary sinus cannula shaped and inserted through a right parasternal mediastinotomy incision to the coronary sinus orifice, according to an embodiment.

FIG. 7C is a diagram 720 illustrating the coronary sinus cannula 600 shaped and inserted through a right parasternal mediastinotomy incision to the coronary sinus orifice, according to an embodiment. The cannula perforates the right atrium within the purse-string suture 710 (or self-sealing system in other embodiments), passes through the right atrium and enters the coronary sinus orifice 704, guided by sensors included in the sensor suite 630, if any. For example, in some embodiments, the tapered tip 626 of cannula 600 is guided into the coronary sinus orifice assisted by tactile feedback with fluoroscopy or echocardiography. The obturator tip (e.g., soft plastic tip 626) enters the coronary sinus far enough that a cardiac end of the hollow shaft 614 of the outer sheath, e.g., tear-away outer sheath 610, lies within the coronary sinus orifice 704.

Figure 7D:
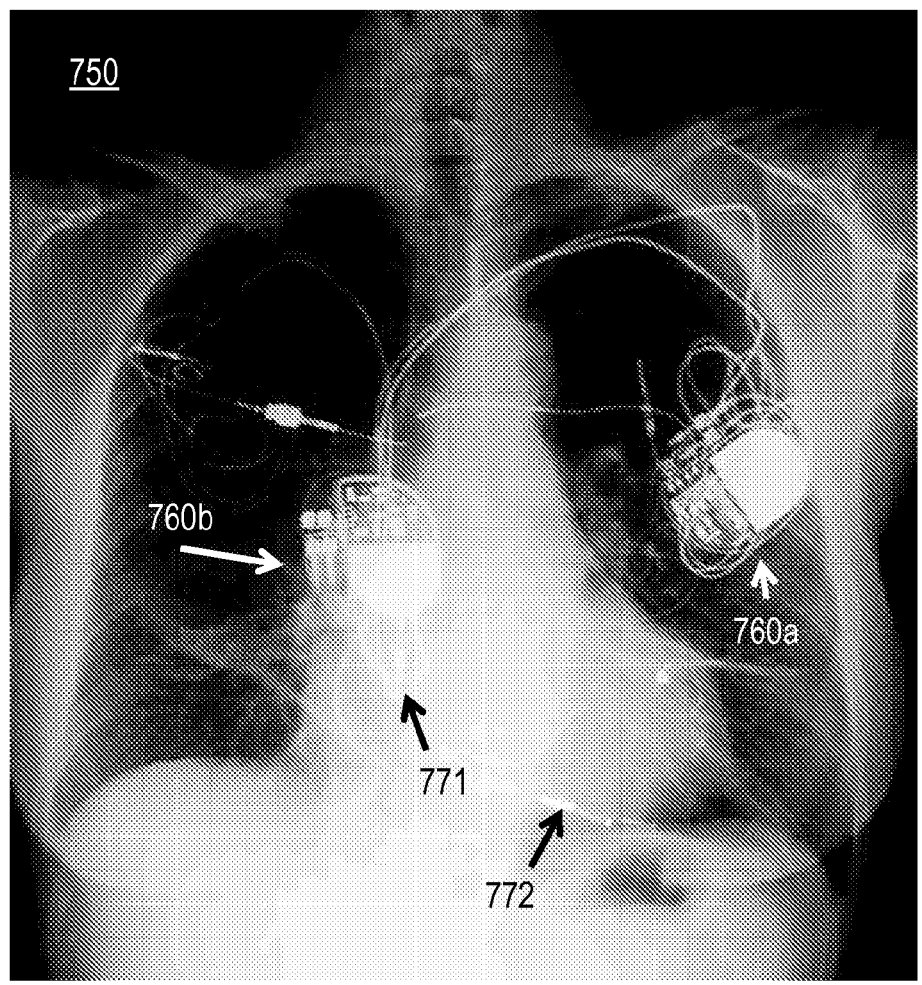
FIG. 7D is an image illustrating placement of two pacemakers in a patient, according to an embodiment.

FIG. 7D is an image 750 illustrating placement of two pacemakers 760a and 760b in a patient, according to an embodiment. Pacemaker 760b was inserted by right parasternal mediastinotomy. Leads 771 and 772 were inserted through a purse-string suture into the right atrium and right ventricle, respectively, using RPMS to access the heart. The device end of the lead was then tunneled to pacemaker 760b.

In some embodiments, additional components are included that would allow the RPMS approach to be used under local anesthesia, or without positive pressure ventilation, or both. In various embodiments, the additional components include one or more of: (1) an echo-guided system for percutaneous right atrial puncture from the parasternal incision location; (2) a self-sealing system for atrial puncture; or (3) an air lock seal at the skin level, or some combination. Component 1 is provided with an acoustic reflector or transmitter in sensor suite 630. Components 2 and 4 are depicted in FIG. 8A and FIG. 8B and FIG. 8C.

FIG. 8A is a diagram illustrating a pressure seal collar 801, according to an embodiment. The pressure seal collar 801 includes a hollow shaft 802 sealed at both ends by valves. The lower end is sealed by a soft seal flange 806a against the skin that allows communication from inside the collar to the pleural space. A second valve 806b at the upper end of the collar forms a seal to retain a pressure difference of up to one atmosphere and can maintain this pressure when perforated by the cannula, by the LV lead, or with no perforation. Any method known in the art may be used to form seals 806a and 806b, such as flexible gels or rubber seals lubricated with sterile gel. Suitable gels are included in GELPORT™ from APPLIED MEDICAL RESOURCES CORPORATION™ of Rancho Santa Margarita, Calif. In some embodiments, a vacuum port 808 is included for attachment to a vacuum line that can be used to retain a pressure difference within the pleural space.

FIG. 8B is a diagram illustrating a modified parasternal coronary sinus cannula 802, according to an embodiment. Cannula 802 includes the cannula 600 inserted through the pressure seal collar 801 across the valve at 806b with enough pressure to open the seal 806a. The seals at 806a and 806b form an air lock connecting the interior of the pressure seal collar with the pleural space. A vacuum hose 809 is attached to the vacuum port 808 to maintain negative pressure in the pleural space in the illustrated embodiment. For example, vacuum port 808 is connected to vacuum hose 809 to maintain intrapleural pressure at minus seven centimeters of water pressure, to prevent lung collapse.

The cannula 802 also includes an atrium wall self-sealing system 810a in an initial configuration. The self-sealing system is releasably attached to the outer sheath at a distance from the cardiac end that corresponds to a distance from the entry point on the atrium wall to the coronary sinus orifice. Upon release, the self-sealing system detaches from the outer sheath and embeds on the wall of the atrium. When the cannula 802 is removed, the self sealing system closes with enough pressure to preclude fluid loss from the atrium of the heart, e.g. with sufficient force to withstand physiological pressures induced by heart contractions. Any method may be used to form the self-sealing system 810 and release it from the cannula 802. For example, the self sealing system can be released by pressure, or by a lever pulled from the device end of the cannula 802, or by an electric pulse sent to the system by a wired or wireless channel.

FIG. 8C is a diagram illustrating a self-sealing system 810b deployed at an atrium wall 890, according to an embodiment. The self-sealing system 810b in the deployed configuration is attached to the atrium wall 890 after release; and allows the hollow shaft 614 of the outer sheath to pass through the self-sealing system. When the cannula 802 is removed, leaving the LV lead, for example, the self-sealing system 810b closes around the LV lead with sufficient force to withstand physiological pressures induced by heart contractions. The self-sealing system in the initial configuration 810a and in the deployed configuration 810b are collectively referenced hereinafter as self-sealing system 810.

Any component may be used for the self sealing system 810. In some embodiments, self sealing plugs for arteriotomies are used. For example, an ANGIO-SEAL™ vascular closure device of ST. JUDE MEDICAL™, Minnetonka, Minn., or an PERCLOSE™ suture device (PERCLOSE, INC™., Redwood City, Calif. is used, alone or in some combination. The Angio-Seal Vascular Closure Device VIP Platform consists of the Angio-Seal VIP device, an insertion sheath, an arteriotomy locator (modified dilator) and a guidewire. The Angio-Seal VIP device is composed of an absorbable collagen sponge and a specially designed absorbable polymer anchor that are connected by an absorbable self-tightening suture. The device seals and sandwiches the arteriotomy between its two primary members, the anchor and collagen sponge. Hemostasis is achieved primarily by the mechanical means of the anchor-arteriotomy-collagen sandwich, which is supplemented by the coagulation inducing properties of the collagen. The Angio-Seal Vascular Closure Device components are not made from latex rubber. The Perclose suture device incorporates two components: a sheath holding one or two pairs of needles connected by a suture loop and a rotating barrel used to facilitate the positioning of the device before needle deployment and to guide the needles during their travel through the subcutaneous track. The device uses a percutaneous means to suture and close the arterial site. Both devices are approved by the U.S. Food and Drug Administration.

Thus the cannula 802 includes a skin level pressure seal collar 801 forming an air tight seal around the outer sheath for maintaining a pressure difference between a pressure in a pericardial space of a subject and ambient pressure outside the subject. This seal is water tight in preferred embodiments. Connection to a negative pressure source maintains the pressure difference. Cannula 802 also includes a self-sealing system 810 disposed on the outer sheath for forming a pressure seal at a right atrium wall around a lead deposited by the cannula.

FIG. 9 is a flow diagram illustrating a method 900 for operating a parasternal coronary sinus cannula to pace a heart with a left ventricle pacing lead, according to an embodiment. Although steps in FIG. 9 are shown in a particular order for purposes of illustration, in other embodiments, one or more steps may be performed in a different order or overlapping in time, in series or in parallel, or one or more steps may be omitted or added, or changed in some combination of ways.

In step 901, access is provided to a right atrium of a heart of a subject, such as an animal or human patient using RPMS. In step 902, a cardiac end of the cannula is localized in the coronary sinus orifice. In step 903, a coronary sinus angiogram is performed to ensure placement of the cardiac end of the cannula. In step 904, a left ventricle (LV) lead is inserted in a branch vein of the coronary sinus. In step 905, the access is closed. In step 906, the subject's heart is paced using the LV lead.

In the illustrated embodiment, step 901 to provide access to the right atrium includes steps 911, 913 and 915. In step 911, a right parasternal mediastinotomy (RPMS) is performed. In some embodiments, the general RPMS is performed during step 911, including placing subject on a fluoroscopy table, administering general anesthesia; applying positive pressure ventilation. A surgical RPMS is performed including a possible cartilage resection and pericardiotomy. A right atrial purse-string suture with snare is inserted at the entrance point of the right atrial appendage. The right atrium is punctured inside the purse-string suture for inserting the cannula.

In some embodiments, the pressure seal collar 802 is installed on the cannula in step 913 so that positive pressure ventilation need not be applied during step 911. In some embodiments, the pressure tent described below with reference to FIG. 10 is installed and used in step 91 instead of the collar. In some embodiments, the self-sealing system 810 is installed on the cannula in step 915 so the purse-string and snare need not be surgically inserted during step 911, allowing the RPMS to be performed laparoscopically with local anesthesia instead of with general anesthesia during step 911.

In the illustrated embodiment, step 902 to localize the cardiac end of the cannula in the coronary sinus orifice includes steps 921 and 923. In step 921 the parasternal coronary sinus cannula is inserted into the right atrium. For example, in some embodiments, cannula 600 is inserted into the surgically punctured right atrium inside the purse-string suture. In some embodiments, cannula 802 is inserted in an RPMS incision and self-sealing system 810 is deployed at the right atrium wall at a point of entry during step 921. In step 923, the tapered tip of the cannula, e.g., soft plastic tip 626 of obturator 620, is guided into the orifice of the coronary sinus, e.g., assisted by tactile feedback with fluoroscopy or echocardiography, or using one or more sensors in sensor suite 630.

In the illustrated embodiment, step 903 to perform a coronary sinus angiogram includes steps 931 and 933. In step 931 the obturator is removed. For example, the obturator 620 is retracted through the device end of the outer sheath, such as tear-away outer sheath 610. In step 933, a coronary sinus angiogram is performed with a balloon catheter, omniopaque dye and a fluoroscope. This is done to ensure that the cardiac end of the outer sheath is in the coronary sinus orifice. In some embodiments, the balloon and dye are included in the obturator 620; and step 933 is performed before step 931. In some embodiments, step 903 is omitted.

In the illustrated embodiment, step 904 to insert a LV lead in a branch vein includes steps 941, 943 and 945. In step 941, the rigid shaped stylet 200 is inserted into the LV lead 320 through the open end of the channel 328 and moved to the cardiac end 324 of the LV lead 320. The shaped lead is then fed, cardiac end first, through the device end of the outer sheath of the cannula, past orifice 392, into coronary sinus 394 and down into a branch vein 396 in the epicardial surface of the left ventricle. In some embodiments, the guidance component 332 at the cardiac end 324 is used with a corresponding guidance system to assist the surgeon in feeding the cardiac end into the appropriate branch vein during step 941.

In step 943, the rigid shaped stylet is removed to fix the LV lead in place. The rigid shaped stylet 200 is retracted through the open end of channel 328 at the device end 322 of the LV lead 320. The removal of the shaped stylet 200 from the cardiac end 324, allows the protuberance 330 to engage the walls of the branch vein 396. This fixes the LV electrode 342 in place in the branch vein 396.

In some embodiments, such as embodiments in which X-ray fluoroscopy is not employed, the stylet is replaced by an over-the-wire guidewire, well known in the art. The over-the-wire guidewire is inserted and used to guide the tip of the LV lead into the branch vein of the coronary sinus during step 941; and the guidewire is removed during step 943. The over-the-wire technique for final positioning is the current standard for endocardial CS lead insertion.

In step 945, the outer sheath is removed leaving the LV lead in place. In some embodiments, the outer sheath is retracted, leaving the LV lead 320 in place, by sliding the outer sheath 610 past the device end 322 of the LV lead 320. Such removal is made possible by an iso-diameter LV lead 320 with a diameter everywhere less than an inner diameter of the outer sheath. This is also permitted by a device end 322 that is removeably connected to the pacing system 450, so that the pacing system 450 does not block the removal of the outer sheath. In some embodiments, the outer sheath is a tear-away outer sheath 610 that is removed by initiating the separation process for the sheath and pulling the two halves past the LV lead and through the RPMS incision. Such embodiments are useful for a cardiac end of the LV lead that is suited for connection to a pacemaker but too large to pass through the inner diameter of the outer sheath.

In the illustrated embodiment, step 905 to close the incisions includes steps 951, 953 and 955. In step 951, the sealing structure in the wall of the atrium is closed. In some embodiments, the purse-string suture 312 is tightened to form suture 412 to prevent fluid leakage from the heart. In some embodiments, the self-sealing system 810 automatically closes around the LV lead, preventing fluid leakage at physiological pressures.

In step 953, the device end of the LV lead is tunneled to a pacing system for the LV lead, such as a permanent or temporary pacemaker, using any method known in the art, such as a lead extender and lead tunneler. In step 955, the pressure collar 801 is removed, if present. In some embodiments, the pressure tent, described below, is removed during step 955. Remaining incisions are closed using multilayer sutures, e.g., at the level of the pericardial sac, cartilage resection, muscles, subcutaneous tissue, and skin. A pursestring suture in the muscles of the chest wall is placed and tied before removing the pressure collar or pressure tent, to preserve intrapleural pressure In step 906, the heart 390 is paced using the pacing system 450 or pacemaker 760 and the LV lead 320, as well as other leads placed in the right atrium and right ventricle (not shown) as is well known in the art. For temporary pacing post surgery, especially post re-operation, step 906 is performed for a limited time, e.g., for 24 hours. For permanent BiVP, step 906 continues for a much longer time (e.g., months and years).

Thus techniques are provided for placement of a left ventricle lead for permanent or temporary BiVP using RPMS instead of open heart (open chest) surgery and using the parasternal coronary sinus cannula.

Parasternal Operation Pressure Tent

In various embodiments, additional components are included that allow the RPMS approach to be used without positive pressure ventilation in lieu of the pressure seal collar 801. These components comprise various embodiments of a surgical pressure tent and are depicted in FIG. 10A through FIG. 10F. In some embodiments, the pressure tent is used for parasternal operations not involving leads or lead insertion. In various embodiments, exchange of leads, introducers, obturators, sensors, and catheters are accomplished without pneumothorax and collapse of the right lung. The proposed pressure tent includes external airlocks at two levels and a suction source to prevent or reverse leakage of air into the pleural space. These embodiments allow percutaneous positioning and exchange of LV, RV, and RA electrodes, for example, with prevailing ventilation, but without pneumothorax or bleeding.

These embodiments involve a surgical pressure tent that maintains pressure in the work space at about −10 centimeters of water (cm H2O). When this communicates with the pleural space, instrumentation will be possible without physiologic compromise due to loss of negative intrapleural pressure. Negative pressure in the tent is maintained by: a pressure seal between an inner chamber and the skin; a pressure seal between the chamber and the atmosphere that allows passage of instruments, catheters and leads; and connection to a negative pressure source (e.g. a Pleurevac or chest bottles) maintaining a negative pressure of about 5 to 10 cm H2O. Some embodiment also include a clear viewing window, or an airlock chamber for passing instruments into the work space, or sealed arm access holes, or smaller sealed access holes for cautery, pacing wires, suction, and similar equipment, or some combination. In some embodiments, the tent is lightweight to avoid compromise of respiration. In some embodiments, the pressure tent is suspended from an overhead arm to avoid excessive pressure on the anterior chest of the patient.

There are a number of important advantages to various embodiments. First, the flexible walls of the tent, in some embodiments, give the surgeons visual confirmation that negative pressure is being maintained, because the walls of the tent will be sucked inward as long as there is negative pressure. Second, in some embodiments, the skin seal is a large ring, about three or four inches in diameter. This provides a larger space to work and even allows a conventional parasternal incision, if that became desirable. Furthermore, in some embodiments, the tent is equipped with sealed ports or sleeves that allow the surgeon's arms (or robot arms) to be placed inside the tent (e.g., with sterile gloves).

FIG. 10A is a block diagram illustrating a plan view of a top surface of a surgical pressure tent 1000 for parasternal insertions, according to an embodiment. The illustrated device 1000 is supported by a frame 1004 that circumscribes a volume roughly a size of a hatbox. In other embodiments, the circumscribed volume is sufficient to accommodate manipulators (such as surgeon hands or robot actuators) to perform a particular surgery. In various embodiments, any solid material may be used for some of or the entire frame 1004, such as metal wire, plastic or wooden rods. Thus, a rigid framework circumscribes a volume sufficient to accommodate manipulators to perform a surgery. In the illustrated embodiment, as mentioned, the circumscribed volume is about the size and shape of a hatbox. In other embodiments, other sizes or shapes, or both, are used, such as oval or rectangular shapes.

The top panel is a rigid material; and, at least a portion is transparent (e.g., made of poly(methyl methacrylate)) to view a surgical port in the bottom of the device (e.g., port 1022 depicted in FIG. 10B). Thus, in some embodiments, the rigid framework includes a top panel comprising a transparent portion that permits a view of the surgical opening. For example, in the illustrated embodiment, half is a transparent view port 1012; and the other half includes an outer door 1014 to provide access to an equipment tray chamber (e.g., chamber 1038 depicted in FIG. 10C and FIG. 10D). The outer door 1014 is attached to the other portions of the top panel by a hinge 1016. The perimeter of the door is airtight when closed, using flexible seals, sufficient to substantively prevent airflow around the outer door 1014 at pressure differences up to about 10 cm H2O. Thus, in some embodiments, the top panel further comprises an outer door that, when open, permits access to at least a portion of the circumscribed volume and, when closed, seals sufficiently to withstand pressure differences of about 10 cm H2O.

The side and bottom walls are formed by a sheet of a flexible material 1002 attached to the frame 1004. In some embodiments, the pressure tent consists of a rigid inner frame covered on sides and bottom with flexible, air tight, transparent plastic. In some embodiments, the materials are chosen for the frame 1004 and sheet of flexible material 1002 such that the tent 1000 is lightweight to avoid compromising respiration of the patient by excessive weight on a chest of the patient if the surgical procedure is prolonged. In some embodiments, the framework includes one or more hooks (not shown) so that the tent 1000 can be suspended from above so that the full weight of the tent is not on the chest of the patient. The sheet of flexible material is attached to the rigid framework, in any manner known in the art, to form an enclosure that is airtight at pressures up to about 10 cm H2O, except for a surgical port in a bottom portion of the pressure tent 1000. Thus, the sheet of flexible material is attached to the framework to prevent airflow into the circumscribed volume except through the surgical opening.

The top panel also includes a pressure hose fitting 1018 so that a pressure difference can be established or maintained, or both, inside the pressure tent 1000, when the surgical port is sealed against a surface, such as the skin of a patient. In other embodiments, the pressure hose fitting is placed elsewhere on an outer surface of the tent, such as attached to a portion of the frame 1004 along a side of the tent. Thus, the pressure hose fitting is configured to allow the circumscribed volume to be connected to an air pump to establish a target pressure inside the circumscribed volume. For example, in some embodiments, a cylindrical connector allows connection to a PLEUR-EVAC™ (of Teleflex Inc, Research Triangle Park, N.C.), chest bottle set, or other system for providing low level suction while allowing a high flow rate for any air leakage.

FIG. 10B is a block diagram illustrating a plan view of a bottom surface of a surgical pressure tent 1000 for parasternal insertions, according to an embodiment. In the illustrated embodiment, the bottom of the tent 1000 consists of a portion of the rigid frame that is a circular rigid frame with radially arrayed posts supporting a central circular surgical port 1022. The surgical port 1022 is edged by a seal 1020, such as a coating of a flexible gel, to form an airtight seal with the skin of a patient, at pressure differences up to about 5 to 10 cm H2O. The port itself is open to allow access to the skin of the patient for surgical procedures. The remainder of the bottom is covered with the flexible material, such as plastic, sealing the circumscribed volume against airflow beginning at the perimeter of the surgical port 1022.

Thus, the pressure tent includes a sheet of flexible material impervious to airflow and having a surgical opening, with a sealing material along a perimeter of the surgical opening. The sheet of flexible material is attached to the framework to prevent airflow into the circumscribed volume except through the surgical opening. The sealing material forms a seal against a skin surface of a patient sufficient to withstand pressure differences up to about 10 cm H2O.

In the illustrated embodiment, the inner diameter of the surgical port 1022 is about 10 cm for allowing surgery to insert leads for cardiac pacing equipment.

FIG. 10C is a block diagram illustrating a plan view of a middle section of a surgical pressure tent 1000 for parasternal insertions, according to an embodiment. This section parallels a floor of an equipment tray chamber 1038 that serves as an inner airlock. The chamber 1038 is separated from the remainder of the circumscribed volume (called the inner chamber 1039 hereinafter) by the vertical wall 1034 and the floor. The inner chamber is the operative portion of the circumscribed volume because the operative portion includes the surgical port 1022. In the illustrated embodiment, the chamber 1038 is hemi-cylindrical with rigid, transparent walls. The chamber 1038 is below the outer door 1014. In the floor of the chamber is an inner door 1032 attached to the floor by hinge 1036. The perimeter of the inner door 1032 is airtight when closed, using flexible seals, sufficient to substantively prevent airflow around the inner door 1032 at pressure differences up to about 10 cm H2O.

The inner door 1032 in the equipment tray chamber 1038 is closed when the outer door 1014 is open to retain low pressure in the inner chamber 1039 over the surgical port 1022. With outer door 1014 open, equipment is placed in equipment tray chamber 1038. Then outer door 1014 is closed and sealed. Then the inner door 1032 is opened to move the equipment to the inner chamber 1039 that includes the surgical port 1022.

FIG. 10D is a block diagram illustrating an elevation view of a side of a surgical pressure tent 1000 for parasternal insertions, according to an embodiment. The sides of the tent consist of a perimeter of hinged vertical posts, attached to (such as covered with) a flexible material 1002 (such as a plastic liner). During use, the flexible material 1002 will tend to collapse inward, as a result of the negative pressure applied. This inward motion of the tent provides visual confirmation that the system is working properly and that inner pressure in the tent is negative relative to ambient room pressure. The equipment tray chamber 1038 is separated from the inner chamber 1039 by a floor with inner door 1032 and wall 1034. Although the floor of the chamber 1038 is depicted at about half the height of the tent 1000, in other embodiments the floor may be higher or lower, and the door 1032 may be on the wall 1034 instead of the floor of the chamber 1038. The seal 1020 and bottom of the tent form an airtight seal up to about 5 to 10 cm H2O against the surface skin 1090 of a patient. Although the surface skin 1090 is depicted for purposes of illustration, it is not part of the pressure tent 1000.

For equipment transfer, the chamber 1038 is accessed externally by releasing a latch to open the outer door 1014. The inner door remains locked as equipment is placed in the chamber 1038. After equipment is placed in the chamber 1038, the outer door 1014 is closed. The hinged inner door 1032 is then unlatched from below to release the equipment into the inner chamber, where the equipment can be used. Thus the inner chamber 1039 comprises an operative portion of the circumscribed volume. In the illustrated embodiment, the outer door 1014 opens superiorly and laterally to provide access that maximizes the size of the equipment that can fit in the chamber 1038. For the same reason, the inner door 1032 opens toward the inner chamber 1039 in the illustrated embodiment. In other embodiments, either or both doors may open in a different direction. Thus, in some embodiments, there is a chamber 1038 within the circumscribed volume. The chamber 1038 has an inner door 1032 that when open permits access to an operative portion 1039 of the circumscribed volume that includes the surgical opening and, when closed, blocks access to the operative portion of the circumscribed volume and seals sufficiently to withstand pressure differences of about 10 cm H2O. The outer door 1014, when open, permits access to the chamber 1038.

In some embodiments, the sheet of flexible material further comprises a plurality of sealed arm access ports to allow access for hands of one or more surgeons while maintaining the pressure differences of about 10 cm H2O. For example, in the illustrated embodiment, the perimeter of the tent includes two arm access ports 1040a and 1040b (collectively referenced as arm access ports 1040 hereinafter). In various other embodiments, six or eight sealed arm access ports with sleeves and gloves surround the device for access by operators. Often only one or two operators (2 or 4 hands) are involved in a surgery, and two to four sealed arm access ports 1040 are sufficient. The surgeon's or robot's arms enter the tent through these ports 1040. In some embodiments, each arm access port 1040 is attached to flexible plastic arm sleeves with gloves at one end and elastic rings where they attach to the vertical side walls of the tent 1000. Each ring is covered with an air tight plastic seal. Puncture of the seal provides access for one gown and glove-covered arm. The elastic ring creates an air tight seal. Such sleeve and glove or sealed openings are well known in the art.

FIG. 10E is a block diagram illustrating an elevation view of a front of a surgical pressure tent for parasternal insertions, according to an embodiment. The front view shows frame members 1004, flexible sheet 1002, open outer door 1014, open inner door 1032, chamber 1038, surgical port seal 1020 and arm access ports 1040. Also depicted in FIG. 10E are sleeve and glove portions 1042a and 1042b of the arm access ports 1040a and 1040b, respectively.

In some embodiments with hinged vertical members of the frame, the structure can be partially collapsed for storage by rotating top and bottom panels in opposite directions. FIG. 10F is a block diagram illustrating an elevation view of a side of a collapsed surgical pressure tent for parasternal insertions, according to an embodiment. In some embodiments, vertical support posts 1006 of frame 1004 include hinges 1008 at top and bottom. These posts 1006 make up a portion of the frame 1004, which maintains height. In the illustrated embodiment, the tent 1000 is partially collapsible for easier storage by rotating the top counterclockwise and the bottom clockwise, which angulates hinges 1008 in the vertical support posts 1006.

In various other embodiments, many alternatives to the illustrated pressure tent are implemented, including both larger and smaller versions. For example, a miniaturized pressure tent is appended to the introducer in FIG. 3A, FIG. 3B and FIG. 3C. Suitable gels for the skin seal 1020 are available, such as used in the GELPORT™ (Applied Medical Resources Corp., of Rancho Santa Margarita, Calif.). In some embodiments, the pressure tent is disposable. In some embodiments, reusable seals are available to cover the arm access ports 1040 that have been punctured.

An example method for using the surgical pressure tent includes the following steps. The patient is placed in supine position on an operating table and prepared with antibiotics and sedation as necessary. The patient's skin is prepped in the surgical area. The surgical area of the chest wall is anesthetized with local anesthesia. The surgical pressure tent 1000 is expanded from its collapsed storage state. One or more surgeons scrub, dress in surgical gowns and put on surgical gloves. A support team lowers the surgical pressure tent 1000 onto the chest of the patient, with the surgical port 1022 centered on the surgical area. The perimeter of the field is covered with sterile drapes. The pressure hose fitting 1018 is connected to a suction source. The arm access ports 1040 are punctured as appropriate by the surgeons. The surgical procedure begins. Surgical equipment is loaded into the equipment tray chamber 1038 as desired. If a surgeon must drop out, reusable seals for the arm access ports 1040 are put in place. After surgery, the surgical pressure tent 1000 is restored for reuse or, if disposable, is discarded.

Data Processing Hardware Overview

Figure 11:
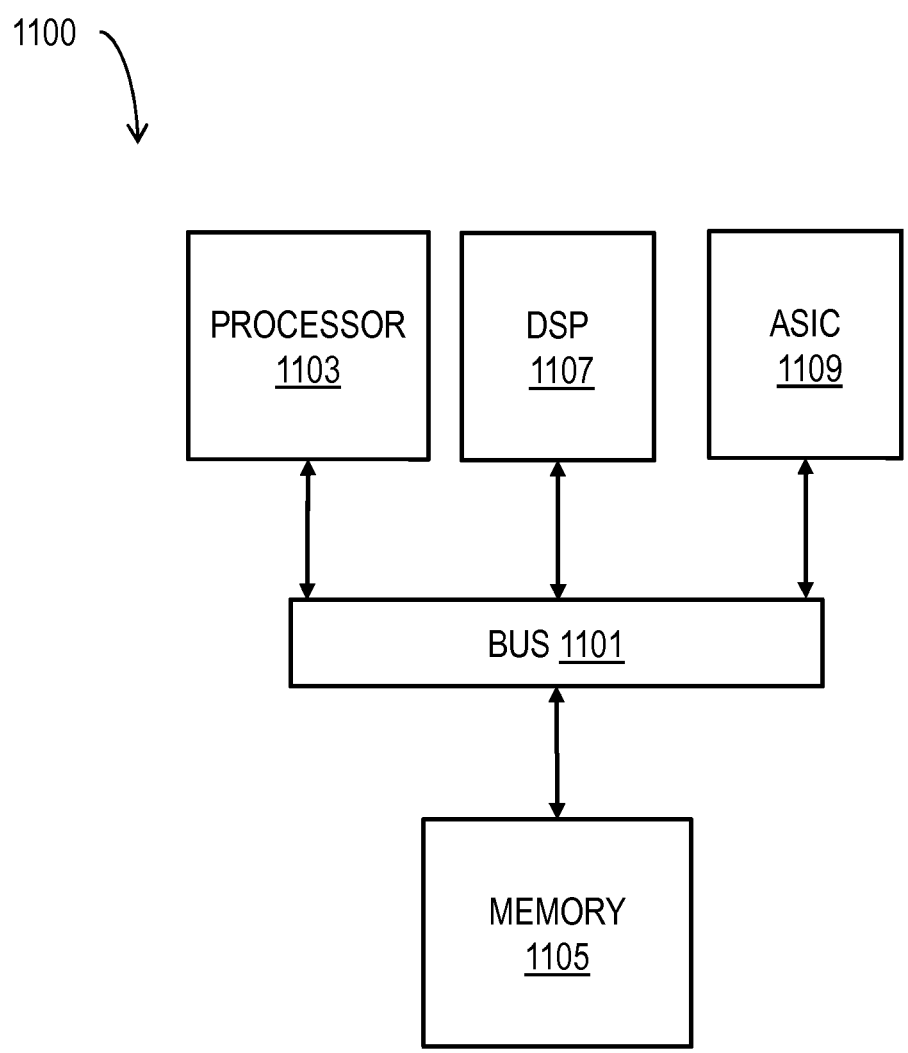
FIG. 11 is a diagram of a chip set that can be used to implement an embodiment of the invention.

FIG. 11 illustrates a chip set 1100 upon which an embodiment of the invention may be implemented. Chip set 1100 is programmed to communicate measurements for a parasternal coronary sinus (CS) cannula as described herein and includes, for instance, processor and memory components incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of communicating measurements for a parasternal CS cannula.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform the inventive steps described herein to communicate measurements for a parasternal CS cannula. The memory 1105 also stores the data associated with or generated by the execution of the inventive steps.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A lead for a pacing electrode comprising:
a hollow tube of flexible material open at a proximal end;
a first electrode at a distal end of the hollow tube;
a first electrical conductor that electrically connects the first electrode to the proximal end and that is positioned within the flexible material; and
a shaped stylet of rigid material inside the hollow tube at the distal end and removable through the open proximal end,
wherein the shaped stylet is curved in a first plane to match a curve of a left ventricle portion of coronary sinus and curved in a different second plane to match a curve of a branch vein of the coronary sinus.

2. A lead as recited in claim 1, further comprising:
a second electrode at the distal end of the hollow tube and spaced apart from the first electrode; and
a second electrical conductor that electrically connects the second electrode to the proximal end and that is positioned within the flexible material apart from the first electrical conductor.

3. A lead as recited in claim 1, wherein the proximal end is configured to be releasably connected physically and electrically to a pacing signal generator.

4. A lead as recited in claim 1, wherein the distal end is configured to hook into a wall of the branch vein when the shaped stylet is retracted through the open proximal end.

5. A lead as recited in claim 1, wherein the hollow tube and first electrode have a diameter less than an inner diameter of a coronary sinus cardioplegia cannula catheter.

6. A lead as recited in claim 1, wherein the hollow tube and first electrode and the second electrode have a diameter less than an inner diameter of a cardioplegia cannula catheter.

7. A lead as recited in claim 1, further comprising at the distal end a probe for a guidance system for at least one of an X-ray fluoroscope guidance system, an echocardiography guidance system, an electrical guidance system, a thermography guidance system, or a radio frequency identification (RFID) guidance system.

8. A kit for a lead for a pacing electrode comprising:
a hollow tube of flexible material open at a proximal end;
a first electrode at a distal end of the hollow tube;
a first electrical conductor that electrically connects the first electrode to the proximal end; and
a shaped stylet of rigid material for insertion and removal through the hollow proximal end to position in the hollow tube at the distal end,
wherein the shaped stylet is curved in a first plane to match a curve of a left ventricle portion of coronary sinus and curved in a different second plane to match a curve of a branch vein of the coronary sinus.

9. A method for placing a left ventricle pacing electrode, comprising:
inserting a coronary sinus cannula catheter through an orifice from a right atrium to a coronary sinus;
feeding a distal end of a left ventricle lead that includes a shaped stylet in a hollow tube through the coronary sinus cannula catheter into the coronary sinus and a branch vein of the coronary sinus;
removing the coronary sinus cannula catheter; and
retracting the shaped stylus,
wherein the left ventricle lead comprises:
the hollow tube made of flexible material and open at a proximal end,
a first electrode at a distal end of the hollow tube;
a first electrical conductor that electrically connects the first electrode to the proximal end and that is positioned within the flexible material; and
the shaped stylet of rigid material inside the hollow tube at the cardiac distal end and removable through the open proximal end, wherein the shaped stylet is curved in a first plane to match a curve of a left ventricle portion of the coronary sinus and curved in a different second plane to match a curve of the branch vein of the coronary sinus.

10. A method as recited in claim 9, wherein inserting the coronary sinus cannula catheter further comprises first performing a parasternal medial sternotomy to gain access to the chest cavity and then inserting the coronary sinus cannula catheter into the right atrium.

11. A method as recited in claim 9, wherein inserting the coronary sinus cannula catheter comprises inserting a cardioplegia cannula catheter during open heart surgery.

12. A method as recited in claim 9, further comprising physically and electrically connecting the proximal end of the lead to a biventricular pacing (BiVP) signal source after removing the coronary sinus cannula catheter.

13. A method as recited in claim 12, further comprising performing biventricular pacing.

14. A method as recited in claim 13, further comprising retracting the LV lead after performing temporary biventricular pacing.

* * * * *